(12) United States Patent
Donovan et al.

(10) Patent No.: US 11,679,020 B2
(45) Date of Patent: Jun. 20, 2023

(54) PERFORATED CHAMBER OSTOMY WAFERS, OSTOMY DEVICES INCLUDING THE SAME, AND METHODS OF APPLYING OSTOMY WAFERS AND OSTOMY DEVICES

(71) Applicant: CONVATEC TECHNOLOGIES INC., Las Vegas, NV (US)

(72) Inventors: Emily Donovan, Deeside (GB); Garry Storey, Deeside (GB); Wayne Bonnefin, Deeside (GB); Roxanna Woodward, Deeside (GB); Stephen Desmond, Deeside (GB); Lisa Price, Deeside (GB); Clive Wilson, Deeside (GB); James Glover, Deeside (GB)

(73) Assignee: ConvaTec Technologies, Inc., Las Vegas, NV (US)

(*) Notice: Subject to any disclaimer, the term of this patent is extended or adjusted under 35 U.S.C. 154(b) by 377 days.

(21) Appl. No.: 16/859,506

(22) Filed: Apr. 27, 2020

(65) Prior Publication Data
US 2020/0337879 A1   Oct. 29, 2020

Related U.S. Application Data

(60) Provisional application No. 62/838,899, filed on Apr. 25, 2019.

(51) Int. Cl.
*A61F 5/443* (2006.01)
*A61F 5/445* (2006.01)
*A61F 5/44* (2006.01)

(52) U.S. Cl.
CPC .............. *A61F 5/443* (2013.01); *A61F 5/445* (2013.01)

(58) Field of Classification Search
CPC ... A61F 5/448; A61F 5/443; A61F 2005/4483
See application file for complete search history.

(56) References Cited

U.S. PATENT DOCUMENTS 4,231,369 A  *  11/1980  Sorensen  .............. A61L 24/043
                                                       604/336
4,834,731 A  *  5/1989   Nowak  .................... A61F 5/448
                                                       604/339
(Continued)

FOREIGN PATENT DOCUMENTS

EP  0686381 A1  12/1995
EP  3643224 A1   4/2020
(Continued)

OTHER PUBLICATIONS

US 10,806,622 B2, 10/2020, Hansen et al. (withdrawn)
(Continued)

*Primary Examiner* — Guy K Townsend
(74) *Attorney, Agent, or Firm* — Taft Stettinius & Hollister LLP; Ryan O. White; Derek B. Lavender

(57) ABSTRACT

Ostomy wafers, ostomy devices incorporating ostomy wafers, and methods of applying ostomy wafers and ostomy devices are disclosed herein. An ostomy wafer may include an external layer and a convex layer coupled to the external layer. An ostomy device may include an ostomy pouch and an ostomy wafer coupled to the ostomy pouch that includes an external layer and a convex layer coupled to the external layer.

29 Claims, 5 Drawing Sheets

(56) References Cited

U.S. PATENT DOCUMENTS

| | | | |
|---|---|---|---|
| 4,973,323 A * | 11/1990 | Kaczmarek | A61F 5/448 604/277 |
| 5,013,307 A * | 5/1991 | Broida | A61F 13/45 604/338 |
| 5,607,413 A * | 3/1997 | Holmberg | A61F 5/448 604/338 |
| 5,718,696 A * | 2/1998 | Kollerup | A61F 5/448 604/338 |
| 5,730,735 A * | 3/1998 | Holmberg | A61F 5/448 604/338 |
| 6,520,943 B1 * | 2/2003 | Wagner | A61F 5/445 604/338 |
| 6,790,200 B2 * | 9/2004 | Fenton | A61F 5/445 604/338 |
| 6,869,422 B2 * | 3/2005 | Fenton | A61F 5/445 604/338 |
| 7,029,464 B2 * | 4/2006 | Fenton | A61F 5/448 604/277 |
| 7,347,844 B2 * | 3/2008 | Cline | A61F 5/448 604/338 |
| 7,857,796 B2 * | 12/2010 | Cline | A61F 5/448 604/277 |
| 8,449,513 B2 * | 5/2013 | Abrams | A61F 5/445 604/342 |
| 8,979,811 B2 | 3/2015 | Keleny et al. | |
| 9,968,480 B2 | 5/2018 | Nyberg | |
| 10,278,857 B2 * | 5/2019 | Hansen | A61F 5/4404 |
| D862,691 S | 10/2019 | Fenton | |
| 10,434,015 B2 | 10/2019 | Taylor et al. | |
| 10,434,309 B2 | 10/2019 | Forsell | |
| 10,449,081 B2 | 10/2019 | Lee | |
| 10,449,082 B2 | 10/2019 | Johnsen | |
| 10,463,527 B2 | 11/2019 | Gallant et al. | |
| 10,470,917 B2 | 11/2019 | Chang | |
| 10,470,918 B2 | 11/2019 | Bendix | |
| 10,471,173 B2 | 11/2019 | Misawa | |
| 10,478,328 B2 | 11/2019 | Guidry et al. | |
| 10,478,329 B2 | 11/2019 | Oberholtzer et al. | |
| 10,478,330 B2 | 11/2019 | Wiltshire et al. | |
| 10,500,084 B2 | 12/2019 | Hansen et al. | |
| 10,500,315 B2 | 12/2019 | Chang et al. | |
| 10,507,318 B2 | 12/2019 | Jin et al. | |
| 10,512,562 B2 | 12/2019 | Kavanagh et al. | |
| 10,524,953 B2 | 1/2020 | Hanuka et al. | |
| 10,531,978 B2 | 1/2020 | Haas et al. | |
| 10,537,461 B2 | 1/2020 | Hanuka et al. | |
| 10,537,462 B1 | 1/2020 | Hatchett et al. | |
| 10,583,029 B2 | 3/2020 | Chang | |
| 10,588,773 B2 | 3/2020 | Tsai et al. | |
| 10,610,402 B1 | 4/2020 | Idowu et al. | |
| 10,617,554 B2 | 4/2020 | Luce | |
| 10,617,555 B2 | 4/2020 | James et al. | |
| 10,646,370 B2 | 5/2020 | Keleny et al. | |
| 10,653,551 B2 | 5/2020 | Apolinario et al. | |
| 10,660,784 B2 | 5/2020 | Nishtala et al. | |
| 10,660,785 B2 | 5/2020 | Kaufman et al. | |
| 10,660,786 B2 | 5/2020 | Obst et al. | |
| 10,729,806 B2 | 8/2020 | Bingol et al. | |
| 10,736,769 B2 | 8/2020 | Grove Sund et al. | |
| 10,744,224 B2 | 8/2020 | Israelson et al. | |
| 10,758,398 B2 | 9/2020 | Murthy Aravalli et al. | |
| 10,779,986 B2 | 9/2020 | Cox | |
| 10,786,652 B2 * | 9/2020 | Doshi | A61F 13/0226 |
| 10,799,385 B2 | 10/2020 | Hansen et al. | |
| 10,813,786 B2 | 10/2020 | Lysgaard | |
| 10,813,787 B2 | 10/2020 | Dinakara et al. | |
| 10,945,873 B2 * | 3/2021 | Fenton | A61F 5/445 |
| 10,973,676 B2 * | 4/2021 | Fenton | A61F 5/448 |
| 11,071,640 B2 | 7/2021 | Fattman et al. | |
| 11,076,979 B2 | 8/2021 | Fattman et al. | |
| 11,077,224 B2 | 8/2021 | Stroebech et al. | |
| 11,090,185 B2 | 8/2021 | Masters et al. | |
| 11,304,842 B2 | 4/2022 | Becker et al. | |
| 11,324,507 B2 | 5/2022 | Aravalli | |
| 11,351,055 B2 | 6/2022 | Jones et al. | |
| 11,357,658 B2 | 6/2022 | Cardell et al. | |
| 11,484,432 B2 * | 11/2022 | Hansen | A61F 5/4404 |
| 2002/0088080 A1 * | 7/2002 | Fenton | A61F 5/445 604/338 |
| 2004/0006320 A1 * | 1/2004 | Buglino | A61F 5/448 604/344 |
| 2004/0106908 A1 * | 6/2004 | Leise, Jr. | A61F 5/448 604/355 |
| 2004/0193122 A1 * | 9/2004 | Cline | A61F 5/448 604/332 |
| 2004/0193123 A1 * | 9/2004 | Fenton | A61F 5/448 604/344 |
| 2004/0230170 A1 * | 11/2004 | Fenton | A61F 5/445 604/336 |
| 2004/0267216 A1 | 12/2004 | Udayakumar et al. | |
| 2006/0058576 A1 | 3/2006 | Davies et al. | |
| 2008/0119804 A1 * | 5/2008 | Cline | A61F 5/445 604/338 |
| 2010/0168693 A1 * | 7/2010 | Edvardsen | A61F 5/451 604/355 |
| 2010/0174253 A1 | 7/2010 | Cline et al. | |
| 2010/0324511 A1 * | 12/2010 | Dove | A61F 5/445 604/338 |
| 2011/0125115 A1 * | 5/2011 | Anders | A61L 28/0015 604/344 |
| 2011/0166539 A1 * | 7/2011 | Eakin | A61F 5/445 604/339 |
| 2011/0218507 A1 | 9/2011 | Andersen et al. | |
| 2012/0041400 A1 | 2/2012 | Christensen | |
| 2012/0109086 A1 | 5/2012 | Tsai | |
| 2012/0136324 A1 | 5/2012 | Hanuka et al. | |
| 2012/0179124 A1 | 7/2012 | Nguyen-Demary et al. | |
| 2012/0232506 A1 * | 9/2012 | Todd | A61F 5/445 604/339 |
| 2013/0060184 A1 * | 3/2013 | Rea | A61F 13/0246 602/54 |
| 2013/0072886 A1 | 3/2013 | Schertiger et al. | |
| 2013/0226063 A1 | 8/2013 | Taylor et al. | |
| 2013/0226116 A1 * | 8/2013 | Edvardsen | A61F 5/443 604/338 |
| 2014/0207094 A1 | 7/2014 | Chang | |
| 2014/0221950 A1 | 8/2014 | Chang et al. | |
| 2014/0288517 A1 | 9/2014 | Tsai et al. | |
| 2014/0316360 A1 * | 10/2014 | Ekfeldt | A61F 5/445 604/338 |
| 2015/0133881 A1 | 5/2015 | Freiding | |
| 2015/0209172 A1 | 7/2015 | Richmann et al. | |
| 2015/0359656 A1 * | 12/2015 | Hansen | A61F 5/443 604/344 |
| 2016/0151198 A1 | 6/2016 | Frampton et al. | |
| 2016/0193003 A1 | 7/2016 | Todd et al. | |
| 2016/0206469 A1 | 7/2016 | Prezelin | |
| 2016/0256665 A1 * | 9/2016 | Doshi | A61F 13/00063 |
| 2017/0007440 A1 | 1/2017 | Moavenian | |
| 2017/0065451 A1 | 3/2017 | Brandt et al. | |
| 2017/0209295 A1 | 7/2017 | Smith et al. | |
| 2017/0209296 A1 | 7/2017 | Cailleteau | |
| 2018/0021164 A1 * | 1/2018 | Fenton | A61F 13/02 604/336 |
| 2018/0021165 A1 * | 1/2018 | Fenton | A61F 5/445 604/338 |
| 2018/0064572 A1 | 3/2018 | Wiltshire | |
| 2018/0134607 A1 * | 5/2018 | Ichikawa | B23K 26/389 |
| 2018/0235801 A1 * | 8/2018 | Oellgaard | A61F 5/445 |
| 2018/0236207 A1 | 8/2018 | Shankarsetty | |
| 2018/0296384 A1 * | 10/2018 | O'Brien | A61F 5/443 |
| 2018/0303655 A1 | 10/2018 | Glithero et al. | |
| 2018/0311066 A1 | 11/2018 | Hansen et al. | |
| 2018/0325718 A1 * | 11/2018 | Ekfeldt | A61F 5/445 |
| 2018/0344506 A1 | 12/2018 | Larsen | |
| 2018/0360644 A1 | 12/2018 | Alvarez Ponce | |
| 2018/0369474 A1 | 12/2018 | Falleboe et al. | |
| 2019/0015241 A1 | 1/2019 | Lin et al. | |
| 2019/0029868 A1 | 1/2019 | Grum-Schwensen et al. | |
| 2019/0110919 A1 | 4/2019 | Beckers et al. | |
| 2019/0117441 A1 * | 4/2019 | Hansen | A61F 5/443 |
| 2019/0117824 A1 | 4/2019 | Hansen et al. | |

(56) References Cited

U.S. PATENT DOCUMENTS

| | | |
|---|---|---|
| 2019/0247549 A1 | 8/2019 | Nielsen |
| 2019/0321213 A1 | 10/2019 | Morrison, Sr. |
| 2019/0328571 A1 | 10/2019 | Adachi |
| 2019/0328572 A1 | 10/2019 | Weinberg et al. |
| 2019/0358076 A1 | 11/2019 | Blatt |
| 2019/0365560 A1 | 12/2019 | Timms et al. |
| 2019/0374372 A1 | 12/2019 | Seres et al. |
| 2019/0380860 A1 | 12/2019 | Eggert et al. |
| 2019/0380861 A1 | 12/2019 | Nordquist et al. |
| 2019/0380882 A1 | 12/2019 | Taylor et al. |
| 2020/0000624 A1 | 1/2020 | Gibbons et al. |
| 2020/0015996 A1* | 1/2020 | Schertiger ............... A61F 5/445 |
| 2020/0030134 A1 | 1/2020 | Hopper |
| 2020/0038226 A1 | 2/2020 | Botten et al. |
| 2020/0038227 A1 | 2/2020 | Makar, Jr. |
| 2020/0038228 A1 | 2/2020 | Aravalli et al. |
| 2020/0038229 A1 | 2/2020 | Aravalli |
| 2020/0046541 A1 | 2/2020 | Sund et al. |
| 2020/0046542 A1 | 2/2020 | Guidry et al. |
| 2020/0046543 A1 | 2/2020 | Scalise et al. |
| 2020/0054476 A1 | 2/2020 | Miller |
| 2020/0054478 A1 | 2/2020 | Forsell |
| 2020/0060863 A1 | 2/2020 | Sund et al. |
| 2020/0061282 A1 | 2/2020 | Hvid et al. |
| 2020/0069455 A1 | 3/2020 | Oberholtzer et al. |
| 2020/0069529 A1 | 3/2020 | Starnes et al. |
| 2020/0078206 A1 | 3/2020 | Chiladakis |
| 2020/0085608 A1 | 3/2020 | Hrushka et al. |
| 2020/0093633 A1 | 3/2020 | Blumrosen et al. |
| 2020/0100931 A1* | 4/2020 | Schoess ................. A61F 5/443 |
| 2020/0100946 A1 | 4/2020 | Wohlgemuth et al. |
| 2020/0121490 A1 | 4/2020 | Woodward et al. |
| 2020/0138618 A1 | 5/2020 | Roszkowiak et al. |
| 2020/0138619 A1 | 5/2020 | Cisko, Jr. et al. |
| 2020/0146944 A1 | 5/2020 | Moulton et al. |
| 2020/0155338 A1 | 5/2020 | Meteer |
| 2020/0163792 A1 | 5/2020 | Schertiger |
| 2020/0164196 A1 | 5/2020 | Jin et al. |
| 2020/0188160 A1 | 6/2020 | Udayakumar |
| 2020/0188161 A1 | 6/2020 | Seres et al. |
| 2020/0188162 A1 | 6/2020 | Menifee |
| 2020/0197213 A1 | 6/2020 | Frampton-Vallance et al. |
| 2020/0214371 A1 | 7/2020 | Apelt |
| 2020/0214872 A1 | 7/2020 | Tretheway et al. |
| 2020/0214873 A1 | 7/2020 | Tretheway et al. |
| 2020/0214875 A1 | 7/2020 | Tretheway et al. |
| 2020/0229962 A1 | 7/2020 | Torstensen et al. |
| 2020/0237550 A1 | 7/2020 | Hussey et al. |
| 2020/0246173 A1 | 8/2020 | Schertiger et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1* | 8/2020 | Hansen ................. A61B 5/4851 |
| 2020/0246178 A1 | 8/2020 | O'Hamill et al. |
| 2020/0253633 A1 | 8/2020 | Obst et al. |
| 2020/0253777 A1* | 8/2020 | Jones ..................... A61F 5/443 |
| 2020/0261254 A1 | 8/2020 | Williams et al. |
| 2020/0276044 A1 | 9/2020 | Tretheway et al. |
| 2020/0276045 A1 | 9/2020 | Bendavit |
| 2020/0281758 A1 | 9/2020 | Tan |
| 2020/0281759 A1 | 9/2020 | Lu |
| 2020/0281761 A1 | 9/2020 | Tretheway et al. |
| 2020/0289307 A1 | 9/2020 | Tretheway |
| 2020/0289308 A1 | 9/2020 | Tretheway et al. |
| 2020/0297524 A1* | 9/2020 | Hunt ...................... A61F 5/445 |
| 2020/0306073 A1 | 10/2020 | Olsen et al. |
| 2020/0306074 A1 | 10/2020 | Speiermann et al. |
| 2020/0330258 A1 | 10/2020 | Hansen et al. |
| 2020/0330259 A1 | 10/2020 | Sund et al. |
| 2020/0330260 A1 | 10/2020 | Hansen et al. |
| 2020/0337879 A1* | 10/2020 | Donovan ................ A61F 5/443 |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0337884 A1* | 10/2020 | Donovan ................ A61F 5/448 |
| 2020/0337885 A1* | 10/2020 | Donovan ................ A61F 5/443 |
| 2020/0338230 A1 | 10/2020 | Israelson et al. |
| 2021/0212856 A1 | 7/2021 | Kelleher et al. |
| 2021/0290426 A1 | 9/2021 | Rea |
| 2021/0316037 A1 | 10/2021 | Stroebech et al. |
| 2021/0353448 A1 | 11/2021 | Fattman et al. |
| 2022/0090720 A1 | 3/2022 | Jin et al. |
| 2022/0125617 A1 | 4/2022 | Botten |
| 2022/0133522 A1 | 5/2022 | Chopra et al. |
| 2022/0151815 A1 | 5/2022 | Nielsen |

FOREIGN PATENT DOCUMENTS

| | | | |
|---|---|---|---|
| EP | 2453852 B1 | 6/2021 | |
| EP | 3488830 B1 | 6/2021 | |
| EP | 3609445 B1 | 6/2021 | |
| EP | 3622923 B1 | 8/2021 | |
| EP | 3937862 A1 | 1/2022 | |
| EP | 3096719 B1 | 2/2022 | |
| EP | 3946178 A4 | 2/2022 | |
| EP | 3958800 A1 | 3/2022 | |
| EP | 3979959 A1 | 4/2022 | |
| EP | 4011337 A1 | 6/2022 | |
| EP | 4011338 A1 | 6/2022 | |
| EP | 4011339 A1 | 6/2022 | |
| GB | 2534012 A | 7/2016 | |
| GB | 2544180 A | 5/2017 | |
| GB | 2548673 A | 9/2017 | |
| GB | 2550936 A | 12/2017 | |
| GB | 2553096 B | 2/2018 | |
| GB | 2570526 A | 7/2019 | |
| GB | 2575687 A | 1/2020 | |
| GB | 2571835 B | 2/2020 | |
| GB | 2594902 A | 11/2021 | |
| GB | 2594903 A | 11/2021 | |
| GB | 2594904 B | 11/2021 | |
| WO | 2007082538 A1 | 7/2007 | |
| WO | WO-2007082538 A1 * | 7/2007 | ......... A61L 24/0031 |
| WO | 2015110544 A1 | 7/2015 | |
| WO | 2015138190 A1 | 9/2015 | |
| WO | 2015148035 A1 | 10/2015 | |
| WO | 2018054442 A1 | 3/2018 | |
| WO | WO-2018054442 A1 * | 3/2018 | ............... A61F 5/44 |
| WO | 2018188706 A1 | 10/2018 | |
| WO | 2018188707 A1 | 10/2018 | |
| WO | 2019058126 A1 | 3/2019 | |
| WO | 2019058127 A1 | 3/2019 | |
| WO | 2019091526 A1 | 5/2019 | |
| WO | 2019091527 A1 | 5/2019 | |
| WO | 2019091528 A1 | 5/2019 | |
| WO | 2019091529 A1 | 5/2019 | |
| WO | 2019091532 A1 | 5/2019 | |
| WO | 2019099662 A1 | 5/2019 | |
| WO | 2019120424 A1 | 6/2019 | |
| WO | 2019120429 A1 | 6/2019 | |
| WO | 2019120430 A1 | 6/2019 | |
| WO | 2019120432 A1 | 6/2019 | |
| WO | 2019120433 A1 | 6/2019 | |
| WO | 2019120434 A1 | 6/2019 | |
| WO | 2019120437 A1 | 6/2019 | |
| WO | 2019120438 A1 | 6/2019 | |
| WO | 2019120439 A1 | 6/2019 | |
| WO | 2019120442 A1 | 6/2019 | |
| WO | 2019120443 A1 | 6/2019 | |
| WO | 2019120444 A1 | 6/2019 | |
| WO | 2019120446 A1 | 6/2019 | |
| WO | 2019120448 A1 | 6/2019 | |
| WO | 2019120449 A1 | 6/2019 | |
| WO | 2019120450 A1 | 6/2019 | |
| WO | 2019120451 A1 | 6/2019 | |
| WO | 2019120452 A1 | 6/2019 | |
| WO | 2019120458 A1 | 6/2019 | |
| WO | 2019197291 A1 | 10/2019 | |
| WO | 2019197971 A1 | 10/2019 | |
| WO | 2019198012 A1 | 10/2019 | |
| WO | 2019221830 A1 | 11/2019 | |
| WO | 2019229267 A2 | 12/2019 | |
| WO | 2019229268 A1 | 12/2019 | |

(56) References Cited

FOREIGN PATENT DOCUMENTS

| | | | |
|---|---|---|---|
| WO | 2019242828 | A1 | 12/2019 |
| WO | 2020008470 | A1 | 1/2020 |
| WO | 2020010766 | A1 | 1/2020 |
| WO | 2020014305 | A1 | 1/2020 |
| WO | 2020016471 | A1 | 1/2020 |
| WO | 2020035121 | A1 | 2/2020 |
| WO | 2020044081 | A1 | 3/2020 |
| WO | 2020055998 | A1 | 3/2020 |
| WO | 2020076607 | A1 | 4/2020 |
| WO | 2020076609 | A1 | 4/2020 |
| WO | 2020084282 | A1 | 4/2020 |
| WO | 2020125906 | A1 | 6/2020 |
| WO | 2020125907 | A1 | 6/2020 |
| WO | 2020128456 | A1 | 6/2020 |
| WO | 2020128457 | A1 | 6/2020 |
| WO | 2020156624 | A1 | 8/2020 |
| WO | 2020156625 | A1 | 8/2020 |
| WO | 2020156626 | A1 | 8/2020 |
| WO | 2020169162 | A1 | 8/2020 |
| WO | 2020173534 | A1 | 9/2020 |
| WO | 2020174218 | A1 | 9/2020 |
| WO | 2020174219 | A1 | 9/2020 |
| WO | 2020174220 | A1 | 9/2020 |
| WO | 2020174497 | A1 | 9/2020 |
| WO | 2020182923 | A1 | 9/2020 |
| WO | 2020193943 | A1 | 10/2020 |
| WO | 2020200382 | A1 | 10/2020 |
| WO | 2020201718 | A1 | 10/2020 |
| WO | 2020216426 | A1 | 10/2020 |
| WO | 2020216427 | A1 | 10/2020 |
| WO | 2020216429 | A1 | 10/2020 |
| WO | 2020219153 | A1 | 10/2020 |

OTHER PUBLICATIONS

International Preliminary Report on Patentability; International Searching Authority; International Application No. PCT/US2020/030091; dated Nov. 4, 2021; 8 pages.

International Search Report; International Searching Authority; International Application No. PCT/US2020/030091; dated Jul. 28, 2020; 2 pages.

Written Opinion of the International Searching Authority, International Searching Authority; International Application No. PCT/US2020/030091; dated Jul. 28, 2020; 7 pages.

Supplementary European Search Report; European Patent Office; European Application No. 20794904.1; dated May 2, 2022; 4 pages.

Communication pursuant to Article 94(3) EPC; European Patent Office; European Application No. 20794904.1; dated May 13, 2022; 5 pages.

\* cited by examiner

PERFORATED CHAMBER OSTOMY WAFERS, OSTOMY DEVICES INCLUDING THE SAME, AND METHODS OF APPLYING OSTOMY WAFERS AND OSTOMY DEVICES

CROSS-REFERENCE TO RELATED APPLICATION

This application claims priority to, and the benefit of, U.S. Provisional Patent Application Ser. No. 62/838,899 entitled "Perforated Chamber Ostomy Device," which was filed on Apr. 25, 2019. That provisional application is incorporated herein by reference in its entirety.

FIELD OF THE DISCLOSURE

The present disclosure relates, generally, to ostomy devices, and, more specifically, to ostomy devices adapted for attachment to a patient.

BACKGROUND

Comfort and security may be primary concerns with regards to the attachment of ostomy devices to a person who has undergone a surgical procedure to create an opening in the body (i.e., ostomate). Attachment features incorporated into, coupled to, or otherwise adapted for use with some ostomy devices may lack a desired degree of comfort and/or conformance. Accordingly, ostomy devices that address those shortcomings remain an area of interest.

SUMMARY

The present disclosure may comprise one or more of the following features and combinations thereof.

According to one aspect of the present disclosure, an ostomy wafer may include an external layer and a perforated convex layer. The external layer may include a stoma channel that extends from the external layer in a direction perpendicular to the radial direction of the external layer. The stoma channel may extend through the perforated convex layer. The external layer and the perforated convex layer may be layered to form a chamber around the stoma channel and within the perforated convex layer to contain a viscous media.

In some embodiments, the perforated convex layer may include a distal rim and a proximal opening to receive the stoma channel.

In some embodiments, the distal rim may contact the external layer to form the chamber.

In some embodiments, the thickness of the perforated convex layer at the proximal opening may be greater than the thickness of the convex layer at the distal rim.

In some embodiments, a width of a distal opening of the perforated convex layer may be greater than a width of the proximal opening of the perforated convex layer.

In some embodiments, the external layer or the perforated convex layer may include an adhesive agent that adheres the wafer to an ostomate.

In some embodiments, the external layer or the perforated convex layer may include a multi-laminate adhesive.

In some embodiments, the external layer or the perforated convex layer may include a multi-laminate adhesive having a molding adhesive, a central film, and a body side.

In some embodiments, the external layer or the perforated convex layer may be moldable.

In some embodiments, the external layer or the perforated convex layer may include Trilam (SH/DH).

In some embodiments, the external layer or the perforated convex layer may include a hydrocolloid adhesive.

In some embodiments, the external layer or the perforated convex layer may include a moldable adhesive barrier.

In some embodiments, the external layer or the perforated convex layer may include a hydrocolloid adhesive.

In some embodiments, the external layer or the perforated convex layer may include a Stomahesive™ seal.

In some embodiments, the ostomy wafer may include a flange or collar attached to the external layer, and the flange or collar may include an adhesive agent.

In some embodiments, the ostomy wafer may include an internal layer that at least partially covers a convex surface of the perforated convex layer and includes an adhesive agent on a stoma-facing side of the internal layer.

In some embodiments, the internal layer may include a skin barrier.

In some embodiments, the ostomy wafer may include a coupling component that couples the wafer to an ostomy pouch.

In some embodiments, the coupling component may mechanically connect to the ostomy pouch.

In some embodiments, the coupling component may adhere the wafer to the ostomy pouch.

In some embodiments, a dimension of the perforated convex layer that is parallel with a direction of effluent flow may be greater than half of a centimeter.

In some embodiments, a dimension of the perforated convex layer that is parallel with a direction of effluent flow may be greater than one centimeter.

In some embodiments, a dimension of the perforated convex layer that is parallel with a direction of effluent flow may be greater than two centimeters.

In some embodiments, the wafer may have a continuous profile, a stepped profile, an inverted profile, or a combination thereof.

In some embodiments, a wafer may have a convex aspect, a concave aspect, a chamfered aspect, or a combination thereof.

In some embodiments, the wafer may have one or more structural elements selected from a wall, a strut, a fin, a column, a tie, and combinations thereof.

In some embodiments, the stoma channel may be tapered.

In some embodiments, the stoma channel may be defined by a stoma channel wall that includes an external structure or an internal structure.

In some embodiments, the viscous media may be an adhesive paste that adheres the wafer to an ostomate.

In some embodiments, the viscous media may be an adhesive solution that adheres the wafer to an ostomate.

In some embodiments, the viscous media may be selected from a gel and a paste.

In some embodiments, the viscous media may include a hydrocolloid.

According to another aspect of the present disclosure, an ostomy device may include any ostomy wafer disclosed herein and an ostomy pouch.

In some embodiments, the wafer may be permanently attached to the ostomy pouch.

In some embodiments, the wafer and the ostomy pouch may be provided as separate pieces before use.

In some embodiments, the ostomy pouch and the ostomy wafer may be attached and subsequently separated without damage to the pouch or the wafer.

According to yet another aspect of the present disclosure, a kit may include any ostomy wafer disclosed herein and a component selected from a viscous media, a pouch, and a combination thereof.

According to yet another aspect of the present disclosure still, a method of applying any ostomy wafer disclosed herein to a subject with a stoma may include placing the ostomy wafer against the subject and manipulating the ostomy wafer to extrude a viscous media through perforations in the ostomy wafer.

According to a further aspect of the present disclosure, an ostomy wafer may include an external layer and a convex layer. The external layer may include a stoma channel to permit the passage of effluent therethrough, and the stoma channel may extend in an axial direction. The convex layer may be coupled to the external layer such that the stoma channel extends therethrough. The convex layer may be formed to include a plurality of perforations that are spaced in a radial direction from the stoma channel and at least one chamber that is in fluid communication with the plurality of perforations and spaced from the stoma channel in the radial direction. The external layer may at least partially close off the at least one chamber to confine viscous media that may be stored in the at least one chamber and distributed through the plurality of perforations to couple the ostomy wafer to a subject in use thereof.

In some embodiments, the external layer may include an annular base and a pedestal extending outwardly therefrom in the axial direction, and the pedestal may at least partially define the stoma channel. The convex layer may include a distal rim and a proximal opening arranged opposite the distal rim, and the convex layer may be coupled to the external layer such that the pedestal extends between the proximal opening and the distal rim. The distal rim may contact the annular base to close off the at least one chamber. Additionally, in some embodiments, a thickness of the convex layer at the proximal opening may be greater than a thickness of the convex layer at the distal rim. In some embodiments still, a thickness of the convex layer at the proximal opening may be less than a thickness of the convex layer at the distal rim. In some embodiments yet still, a width of the proximal opening may be less than a width of a distal opening defined by the distal rim.

In some embodiments, at least one of the external layer and the convex layer may include an adhesive to adhere the ostomy wafer to the subject. The adhesive may include a multi-laminate adhesive.

In some embodiments, at least one of the external layer and the convex layer may include Trilam (SH/DH). Additionally, in some embodiments, at least one of the external layer and the convex layer may include a hydrocolloid adhesive. In some embodiments still, at least one of the external layer and the convex layer may include an adhesive that is moldable complementary to a shape of a stoma of the subject.

In some embodiments, at least one of the external layer and the convex layer may include a Stomahesive™ seal. Additionally, in some embodiments, the stoma channel may include a structure located on an internal surface of the ostomy wafer that defines the stoma channel, and the structure may include a plurality of angled fins that extend toward a stoma and are shaped to mate with the stoma of the subject. In some embodiments still, the stoma channel may include a structure located interiorly of an internal surface of the ostomy wafer that defines the stoma channel, and the structure may be shaped to mate with a stoma of the subject. In some embodiments yet still, the convex layer may extend in a dimension parallel to a flow of effluent through the ostomy wafer over more than half a centimeter.

In some embodiments, the ostomy wafer may have a continuous profile, a stepped profile, an inverted profile, or a combination thereof. The ostomy wafer may have a convex aspect, a concave aspect, a chamfered aspect, or a combination thereof. The ostomy wafer may have one or more structural features selected from a strut, a fin, a column, a tie, and combinations thereof.

In some embodiments, the ostomy wafer may include an internal layer that at least partially covers an exterior of the convex layer that faces the subject, and the internal layer may include a moldable adhesive material. The internal layer may include a second plurality of perforations through which viscous media may be distributed to couple the ostomy wafer to the subject.

In some embodiments, the viscous media may be selected from a gel and a paste. Additionally, in some embodiments, the viscous media may include a hydrocolloid. In some embodiments still, the viscous media may include an adhesive solution that adheres the wafer to the subject.

According to a further aspect of the present disclosure, an ostomy device may include an ostomy pouch and an ostomy wafer coupled to the ostomy pouch. The ostomy wafer may include an external layer and a convex layer. The external layer may include a stoma channel to permit the passage of effluent therethrough, and the stoma channel may extend in an axial direction. The convex layer may be coupled to the external layer such that the stoma channel extends therethrough. The convex layer may be formed to include a plurality of perforations that are spaced in a radial direction from the stoma channel and at least one chamber that is in fluid communication with the plurality of perforations. The external layer may at least partially close off the at least one chamber to confine viscous media that may be stored in the at least one chamber and distributed through the plurality of perforations to couple the ostomy wafer to a subject in use thereof.

In some embodiments, the external layer may include an annular base and a pedestal extending outwardly therefrom in the axial direction that at least partially defines the stoma channel, the convex layer may include a distal rim and a proximal opening arranged opposite the distal rim, and the convex layer may be coupled to the external layer such that the pedestal extends between the proximal opening and the distal rim. Additionally, in some embodiments, the external layer may include an annular base and a pedestal extending outwardly therefrom in the axial direction that at least partially defines the stoma channel, the convex layer may include a distal rim and a proximal opening arranged opposite the distal rim, and the distal rim may contact the annular base to close off the at least one chamber. In some embodiments still, the stoma channel may include a structure located on an internal surface of the ostomy wafer that defines the stoma channel, and the structure may include a plurality of angled fins that extend toward a stoma and are shaped to mate with the stoma of the subject.

In some embodiments, the stoma channel may include a structure located interiorly of an internal surface of the ostomy wafer that defines the stoma channel, and the structure may be shaped to mate with a stoma of the subject. Additionally, in some embodiments, the ostomy wafer may include an internal layer that at least partially covers an exterior of the convex layer that faces the subject, the internal layer may include a moldable adhesive material, and the internal layer may include a second plurality of perforations through which viscous media may be distributed to couple the ostomy wafer to the subject. In some embodiments still, the convex layer may include a distal rim and a proximal opening arranged opposite the distal rim, and a thickness of the convex layer at the proximal opening may be greater than a thickness of the convex layer at the distal rim. In some embodiments yet still, the convex layer may include a distal rim and a proximal opening arranged opposite the distal rim, and a thickness of the convex layer at the proximal opening may be less than a thickness of the convex layer at the distal rim.

According to a further aspect of the present disclosure, a method of applying an ostomy wafer to an ostomate may include positioning a convex layer of the ostomy wafer that includes a plurality of perforations relative to a stoma of the ostomate, pressing the convex layer against the stoma and skin of the ostomate surrounding the stoma, manipulating the convex layer to apply a viscous media to the skin through the plurality of perforations, forming a seal around the stoma with the convex layer, contacting the convex layer with an external layer of the ostomy wafer, and securing the external layer to the ostomate.

In some embodiments, manipulating the convex layer may include adhering the convex layer to the skin with the viscous media. Additionally, in some embodiments, manipulating the convex layer may include adding viscous media to at least one chamber formed in the convex layer so that the added viscous media may be applied through the plurality of perforations. In some embodiments still, pressing the convex layer against the stoma and the skin may include molding the convex layer complementary to a shape of the stoma. In some embodiments yet still, pressing the convex layer against the stoma and the skin may include positioning a stoma channel of the ostomy wafer around the stoma and securing the stoma channel to the stoma using a plurality of angled fins formed on an internal surface of the ostomy wafer that defines the stoma channel.

In some embodiments, pressing the convex layer against the stoma and the skin may include positioning a stoma channel of the ostomy wafer around the stoma and securing the stoma channel to the stoma using a plurality of structures located interiorly of an internal surface of the ostomy wafer that defines the stoma channel. Additionally, in some embodiments, pressing the convex layer against the stoma and the skin may include contacting the ostomate with an internal layer of the ostomy wafer that at least partially covers the convex layer and adhering the internal layer to the ostomate. In some embodiments still, pressing the convex layer against the stoma and the skin may include contacting the ostomate with an internal layer of the ostomy wafer that at least partially covers the convex layer, and manipulating the convex layer may include applying viscous media to the skin through a second plurality of perforations formed in the internal layer.

These and other features of the present disclosure will become more apparent from the following description of the illustrative embodiments.

BRIEF DESCRIPTION OF THE DRAWINGS

The invention described herein is illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

DETAILED DESCRIPTION

Figure 1:
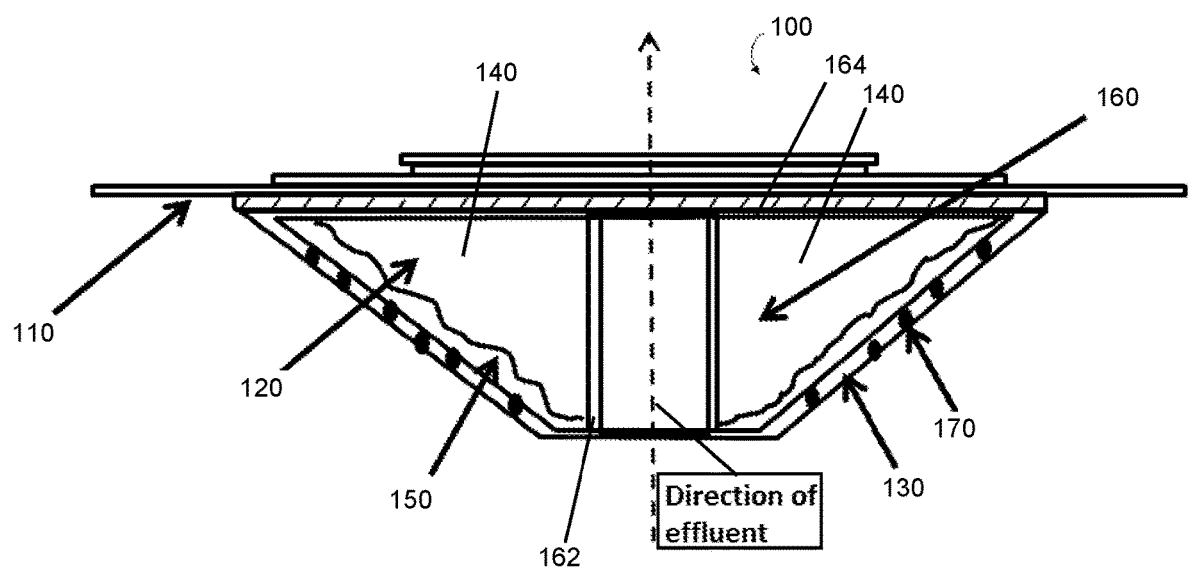
FIG. 1 illustrates a cross-sectional view of one embodiment of a perforated chamber ostomy wafer.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

A number of features described below may be illustrated in the drawings in phantom. Depiction of certain features in phantom is intended to convey that those features may be hidden or present in one or more embodiments, while not necessarily present in other embodiments. Additionally, in the one or more embodiments in which those features may be present, illustration of the features in phantom is intended to convey that the features may have location(s) and/or position(s) different from the locations(s) and/or position(s) shown.

Ostomy wafers of the present disclosure include one or more chambers to contain a viscous media for distribution and/or extrusion through perforations in the ostomy wafers during use. As used herein, the term "chamber" may refer to discrete areas and/or partitioned sections of larger areas, such as the inner space of a convex layer of any ostomy wafer disclosed herein, for example. The chambers contemplated herein may contain, or may be capable of containing, a viscous media. The ostomy wafers disclosed herein may also include one or more perforations in communication with the chamber(s). The ostomy wafers disclosed herein generally include a convex layer and, at least in some embodiment, an internal layer, and the convex layer and/or the internal layer may be perforated. In some instances, the convex layer may be referred to herein as a perforated convex layer and the internal layer may be referred to as a perforated internal layer.

Ostomy wafers disclosed herein may generally be applied quickly without matching up or removing separate or loose elements. The ostomy wafers disclosed herein generally require few steps to apply. In some cases, in a single step, any ostomy wafer disclosed herein may be provided to the user with a chamber already filled with viscous media.

Ostomy wafers disclosed herein generally require minimal dexterity and visual capability in use thereof. In some embodiments, ostomy wafers disclosed herein do not include or require separate or removable elements, which inclusion or requirement might pose a challenge to users with dexterity issues and/or visual issues. In some cases, those users might accidentally leave a removable element in place and/or misuse it.

Ostomy wafers disclosed herein are generally simple for users to use with minimal instruction. Typically, users only apply the ostomy wafer to their skin, possibly with some degree of molding/flexing thereof to accommodate their skin topography. In general, the application of any ostomy wafer disclosed herein includes applying pressure to the chamber to cause viscous media to exit perforations and seal skin to the wafer.

In general, ostomy wafers disclosed herein do not include disposable elements, other than the ostomy wafer itself following use, that is. Thus, ostomy wafers disclosed herein may generate less waste than many devices having other configurations.

FIG. 1 shows an ostomy wafer 100 that includes an external layer 110, a perforated convex layer 120, and, at least in some embodiments, a perforated internal layer 130. The inner space of the convex layer defines a chamber 140 for containing viscous media 150 (e.g., a paste or gel). A stoma channel 160 located within the chamber 140 extends from a proximal opening 162 to a distal opening 164. In some embodiments, the perforated internal layer 130 at least partially surrounds the perforated convex layer 120. When the wafer 100 is compressed to the patient's abdomen, the viscous media 150 seeps out of perforated holes (e.g., the holes or perforations 170 formed in the convex layer 120 and/or the internal layer 130), thereby filling skin indentations of peristomal skin and adhering the wafer 100 to the patient, at least in some embodiments.

In some embodiments, application of the ostomy wafer to the stoma/ostomate may include extruding the viscous media through the perforations. Additionally, in some embodiments, the viscous media may passively seep through the perforations after application of the ostomy wafer. In some embodiments still, the chamber(s) and/or the perforations may distribute the viscous media to the area surrounding the stoma and/or the area around the ostomy wafer. Consequently, in such embodiments, the viscous media may fill creases and folds in the topography of the skin surrounding the stoma to establish an effective barrier to effluent leakage.

In some embodiments, the ostomy wafers disclosed herein may be moldable. Additionally, in some embodiments, at least a portion of the ostomy wafer may be moldable. In some embodiments still, the ostomy wafers disclosed herein may include a three-dimensional (3-D) moldable technology. That moldability may allow for additional customization, adaptation, and conformation beyond that provided by the viscous media.

The ostomy wafers disclosed herein may be adjusted to fit a variety of stoma/peristomal skin shapes, conditions, and sizes. The ostomy wafers of the present disclosure are directed to provide a better fit for ostomates and, at least in some cases, moldability to irregular skin contours and folds in addition to the stoma. The ostomy wafers disclosed herein may be especially useful for a stoma adjacent to very pronounced skin irregularities and/or very uneven skin contours. The ostomy wafers herein may also be especially useful for a subject that has recently undergone surgery, due at least in part to their ability to adapt and conform to the patient's abdomen with minimum pressure during application. The ability of ostomy wafers disclosed herein to conform to the stoma and surrounding skin may improve patient comfort, peace of mind, and quality of life.

The ostomy wafers disclosed herein may be moldable and adaptable to stomas and surrounding skin without requiring physical modification to achieve an appropriate and effective fit. Consequently, when compared to the use and application of other devices, a patient may use and apply the ostomy wafers of the present disclosure with confidence of a lower likelihood of embarrassing leakage, infection, and leakage-related skin damage. Additionally, due at least in part to the moldability, designs, and features thereof, the ostomy wafers of the present disclosure may minimize application time for an array of users and make application easier for nurses and patients. This may be desirable for ostomates because application and removal of ostomy skin barrier products can be a time-consuming process.

The ostomy wafers of the present disclosure include at least one chamber (e.g., the chamber 140) to contain any viscous media disclosed herein. In one example, a first chamber immediate to the perforated convex layer (e.g., the convex layer 120) may contain a first compliant viscous media (e.g., one viscous media 150). Alternatively or additionally, a second chamber immediate to the stoma channel or aperture (e.g., the stoma channel 160 through which effluent flows and any opening(s) associated therewith) may also contain a second compliant viscous media (e.g., another viscous media 150). In some embodiments, the first compliant viscous media and the second compliant viscous media may be the same. In other embodiments, the first compliant viscous media and the second compliant viscous media may be different from one another. In any case, the viscosity of the viscous media may be relatively high and/or "honey-like" at room temperature. Of course, it should be appreciated that use of heat prior to application to the abdomen may decrease the viscosity of the substance, if needed.

In some embodiments, the ostomy wafers contemplated herein may include, or otherwise be supported by, a combination of structural elements (such as struts, fins, and ties, for example) with material properties (e.g., Young's modulus, creep, and stress relaxation values) to confer physical support and controlled deformation. In some embodiments, the gross diameter of the wafer typically ranges up to about 200 mm, and the height of the ostomy wafer typically ranges from about 3 mm to about 30 mm. Additionally, in some embodiments, the stoma channel may fit stomas ranging in an average diameter from about 10 mm to about 100 mm.

Advantages of the ostomy wafers disclosed herein relative to other configurations of ostomy devices include a leakage barrier with improved effectiveness due to the combined moldability and convexity of the ostomy wafer (e.g., the convex layer 120), which allows the ostomy wafer to mold to a stoma and accompany irregular skin contours and folds. Thus, the ostomy wafers disclosed herein may provide an improved seal against effluent on the skin to minimize skin irritation and breakdown. It should be appreciated that minimizing the risk of leakage also helps an ostomate feel more confident in his or her ability to manage his or her stoma. In some embodiments, the 3-D moldable technology of the ostomy wafers presented herein may reduce risks of leakages and consequent infection, as well as user distress and discomfort, at least relative to other ostomy wafer configurations. The barrier of any ostomy wafer disclosed herein may include, or otherwise be established by, the external layer, the convex layer, the internal layer, any additional layer(s), portions thereof, and any combinations thereof.

Generally, the ostomy wafers disclosed herein include a primary interface seal that contacts the base of the ileum or the perimeter of the stoma to lessen the likelihood of effluent seeping underneath skin barriers of the ostomy wafers. In addition, the ostomy wafers disclosed herein may be molded to conform to the surrounding peristomal skin and thereby improve the seal to the peristomal skin surface. Thus, the ostomy wafers of the present disclosure may have a conformable design and/or construction to achieve a seal and exhibit malleability and adaptability to their external environment. The primary interface seal of the ostomy wafers contemplated herein may include, or otherwise be established by, the external layer, the convex layer, the inner layer, any additional layer(s), portions thereof, and any combinations thereof. In some embodiments, the primary interface seal and the skin barrier may be the same. In other embodiments, the primary interface seal may be the only part of the ostomy wafer that seals (e.g., resists effluent leakage) the wafer to the ostomate.

The ostomy wafers of the present disclosure are capable of molding to an individual via multiple mechanisms. In one respect, the compliant perforated internal layer (e.g., the internal layer 130), and subsequent inner chambers defined at least partially by the internal layer, are able to conform to the unique surface features of the individual. In another respect, the exuded viscous media may flow into any unfilled areas between the user and the ostomy wafer and function thereby as a sealant. In some embodiments, the viscous media may be embodied as, or otherwise include, a low modulus sealant that provides compliance during a range of activities of daily living (e.g., bending over, walking, lying pronate, and sitting). The conformity and sealant functions may occur at both the skin-wafer interface and the stoma-wafer interface, at least in some embodiments. The ostomy wafer may also include a number of structural features to aid in the establishment of an effective seal at those interfaces (such as a tapered stoma canal, deformable internal structures, and surface profile features, for example). The ostomy wafer may also incorporate moldable technologies to achieve controlled and/or tailored structural deformations to further enhance the seal at the stoma-wafer interface.

While the ostomy wafers disclosed herein are especially advantageous for the management of flush or retracted stomas, the ostomy wafers of the present disclosure may be used for protruding stomas as well. Generally, a protruding stoma is characterized by internal tissue (e.g., ileum) protruding from a surgical opening beyond the surface of surrounding external skin. A flush stoma may be described as protruding internal tissue that is surrounded by skin such that the distal end of the protruding internal tissue is flush with the surrounding skin. Thus, the protruding tissue does not extend beyond the surface of the surrounding skin in the case of a flush stoma. A retracted stoma may be characterized by an absence of protruding internal tissue. In the case of a retracted stoma, the internal tissue does not protrude beyond the perimeter of the stoma or the skin surrounding the stoma.

In the case of a flush stoma, the ostomy wafer may be pressed into and/or against the stoma such that the opening (e.g., the proximal opening 162 of the stoma channel 160) of the convex layer surrounds the internal tissue. In some cases, the peristomal skin may be at least partially surrounded by, and/or buried in, the convex layer. In the case of a retracted stoma, the convex layer may be pressed into or against the stoma such that the convex layer is at least partially surrounded by, or buried in, the peristomal skin without the opening of the convex layer surrounding any internal tissue.

Certain Terminologies

Unless defined otherwise, all technical and scientific terms used herein are intended to have, or otherwise employ, the same meaning as would be commonly understood by one of ordinary skill in the art to which the subject matter of the present disclosure belongs. It should be appreciated that the foregoing general description and the following examples are exemplary and explanatory only and not restrictive of any subject matter claimed. The use of a singular form herein includes a plural form unless specifically stated otherwise. More specifically, as used in the specification and the appended claims, the singular forms "a," "an" and "the" include plural referents unless the context clearly dictates otherwise. The use of "or" in the present disclosure means "and/or" unless stated otherwise. Furthermore, use of the terms "comprising" and "including" as well as other forms (e.g., "comprise," "comprises," "include," and "includes") is not intended to be limiting.

As used herein, ranges and amounts may be expressed as "about" a particular value or range. The term "about" may also include the exact amount. For example, the expression "about 5 µL" means "about 5 µL" and also "5 µL." Generally, the term "about" includes an amount that would be expected to be within experimental error. More specifically, the term "about" includes values that are within 10% less than to 10% greater than the specified value. In one example, the expression "about 50%" means "between 45% and 55%." In another example, the expression "about 30" means "between 27 and 33."

As used herein, the terms "individual(s)", "subject(s)," and "patient(s)" refer to any mammal. In some embodiments, the mammal may be a human. Of course, it should be appreciated that in other embodiments, the mammal may be a non-human.

For the purposes of the present disclosure, the term "stoma" refers to an opening in the body. Generally, the stoma is a surgical opening in the torso of the body. In some instances, the term "stoma" may also refer to internal tissue, organs, or portions thereof that are exposed by the opening. By way of non-limiting example, internal tissue and/or organs may be selected from the colon, ileum, small intestine, large intestine, jejunum, and duodenum, and combinations thereof. The internal tissue may be an end or a loop of a small or large intestine, for example.

Unless specified otherwise, the term "flush/retracted skin" as used herein refers to any skin surrounding the stoma or opening, whether it be external skin, peristomal skin, or a combination thereof. For the purposes of the present disclosure, the term "external skin" refers to skin that is near the stoma but generally not in contact with internal tissues or effluent. As used herein, the term "peristomal skin" refers to skin that is in contact with internal tissues and/or effluent or skin that is likely to contact effluent.

As used herein, the term "ostomate" refers to a subject that may have use of the ostomy wafers of the present disclosure. While the term "ostomate" typically refers to a subject with a surgical opening, as used herein, the term "ostomate" may refer to a subject who has a stoma, regardless of whether the stoma was created by surgery or other means.

The term "ostomy wafer" may be used interchangeably herein with the terms "adapter," "wafer," "perforated convex wafer," "perforated chamber wafer," and "three-dimensional moldable adapter." Generally, the term "wafer" refers collectively to at least an external layer and a convex layer of the ostomy wafer. Unless otherwise specified, those terms may be used interchangeably. The term "effluent" refers to any internal fluid(s) produced by an ostomate that may be secreted from the stoma or that may exit the stoma.

The devices disclosed herein are adapted for use with a gastrointestinal stoma, at least in some embodiments. Additionally, in some embodiments, the devices disclosed herein may be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. In some embodiments still, the devices disclosed herein may be used with additional devices including, but not limited to, a shunt, a catheter, a plug, or a fecal management system.

It should be appreciated that the section headings contained herein are employed for organization purposes only. As such, the section headings should not be construed as limiting the subject matter described.

Perforated Chamber Wafers

In some embodiments, the ostomy wafers of the present disclosure include an external layer (e.g., the external layer 110) having a stoma channel (e.g., the stoma channel 160) that extends from the external layer in a direction perpendicular to (e.g., an axial direction) a radial direction of the external layer. Additionally, in such embodiments, the ostomy wafers disclosed herein include a perforated convex layer (e.g., the convex layer 120) through which the stoma channel extends. Furthermore, in such embodiments, the external layer and the convex layer are layered to form a chamber (e.g., the chamber 140) around the stoma channel and within the convex layer to contain a viscous media (e.g., the media 150). These ostomy wafers may be referred to herein as "perforated chamber wafers" as indicated above.

Figure 5:
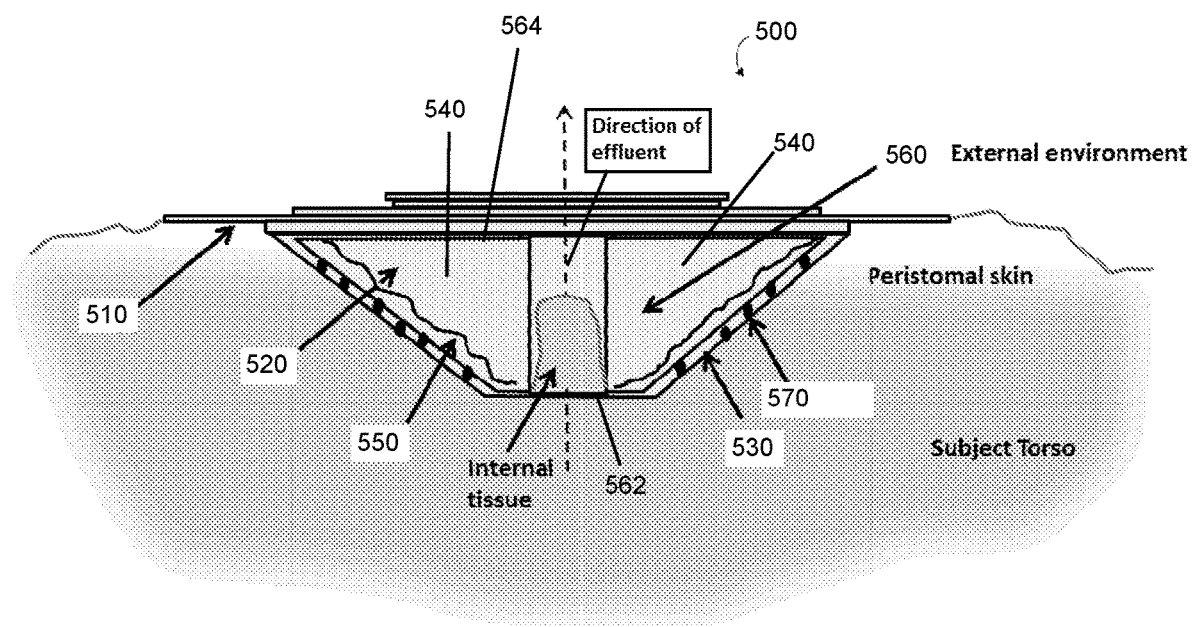
FIG. 5 illustrates a cross-sectional view of a perforated chamber ostomy wafer attached to a stoma of an ostomate.

FIGS. 1 and 5 show respective ostomy wafers 100, 500 with, respectively, external layers 110, 510, perforated convex layers 120, 520, and perforated internal layers 130, 530. The inner spaces of the convex layers 120, 520 define corresponding chambers 140, 540 (which may be referred to as cores) to contain viscous media 150, 550. Stoma channels 160, 560 located within the chambers 140, 150 extend from corresponding proximal openings 162, 562 to corresponding distal openings 164, 564. The perforated internal layers 130, 530 at least partially surround the respective perforated convex layers 120, 520. When the wafers 100, 500 are compressed to the patient's abdomen, the media 150, 550 seeps out of the perforated holes 170, 570 of the layers 120, 520 and the layers 130, 530, thereby filling skin indentations of peristomal skin, at least in some embodiments.

In some embodiments, the layers of any ostomy wafer disclosed herein (e.g., the perforated convex layer) may be generally flat before use (e.g., as shipped). The user may mold the ostomy wafer to the degree of convexity required to accommodate the stoma. Thus, the chamber of the convex layer may be created by the molding of the ostomy wafer, at least in some embodiments. The convex layer may have a cylindrical shape, a cupped shape, a bowl shape, a funneled shape, a tubular shape, an irregular shape, or another suitable geometric form. In some embodiments, the user may apply the viscous media to the chamber of the ostomy wafer after molding the ostomy wafer (e.g., filling the "bowl" of the convex layer). In other embodiments, the user may apply the viscous media to the chamber of the ostomy wafer before molding the ostomy wafer.

In some embodiments, the convex layer may be provided in a form that has a desired degree of convexity such that molding by a user is not required. Additionally, in some embodiments, the convex layer may not be moldable. In some embodiments still, the convex layer may have minimal or negligible moldability. In some embodiments yet still, the ostomy wafer may be provided with a convex layer already containing viscous media in its chamber.

In some embodiments, the perforated convex layer may be described as having a proximal opening (e.g., the opening 162 at a base of a "bowl" defined by the convex layer 120) and a distal opening (e.g., the opening 164 at a "rim" of the bowl defined by the convex layer 120). The convex layer may be thicker near the distal opening than the proximal opening, at least in some embodiments. In one example, the thickness of the convex layer near the proximal opening may be up to 50% of the thickness of the convex layer near the distal opening. The chamber wall may be thicker near the proximal opening than the distal opening, in some embodiments. Additionally, in some embodiments, the thickness of the chamber wall may vary between 0.5 mm to 10 mm. The distal opening may be concentric with the opening(s) of the external and/or internal layers, at least in some embodiments. In other embodiments, the distal opening may be non-concentric with the opening(s) of the external and/or internal layers. The distal opening may be joined with the opening(s) of the external and/or internal layers and/or indistinguishable from the opening(s) of the external and/or internal layers, at least in some embodiments.

Figure 2:
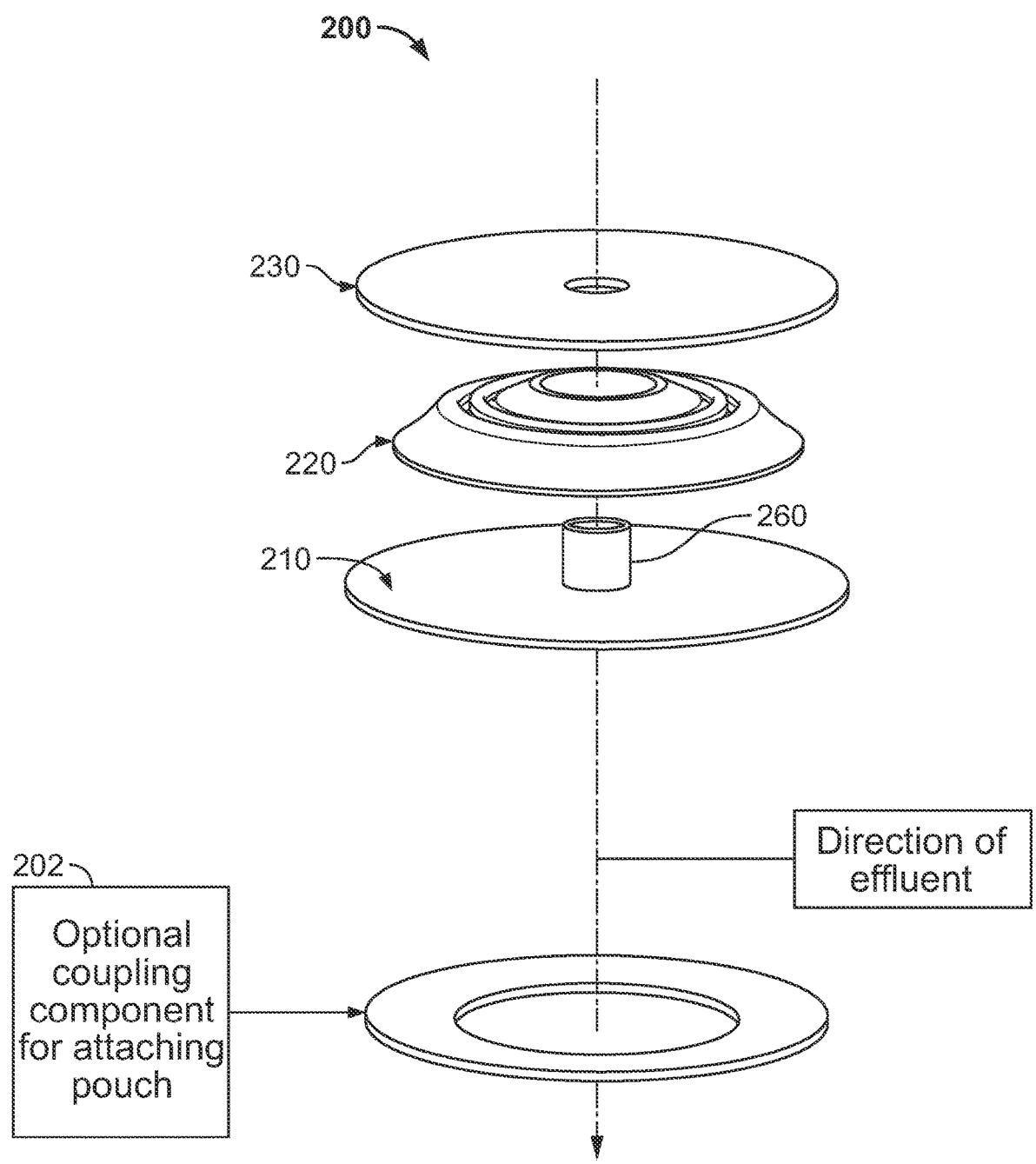
FIG. 2 illustrates an exploded assembly view of one embodiment of a perforated chamber ostomy wafer.
Figure 3:
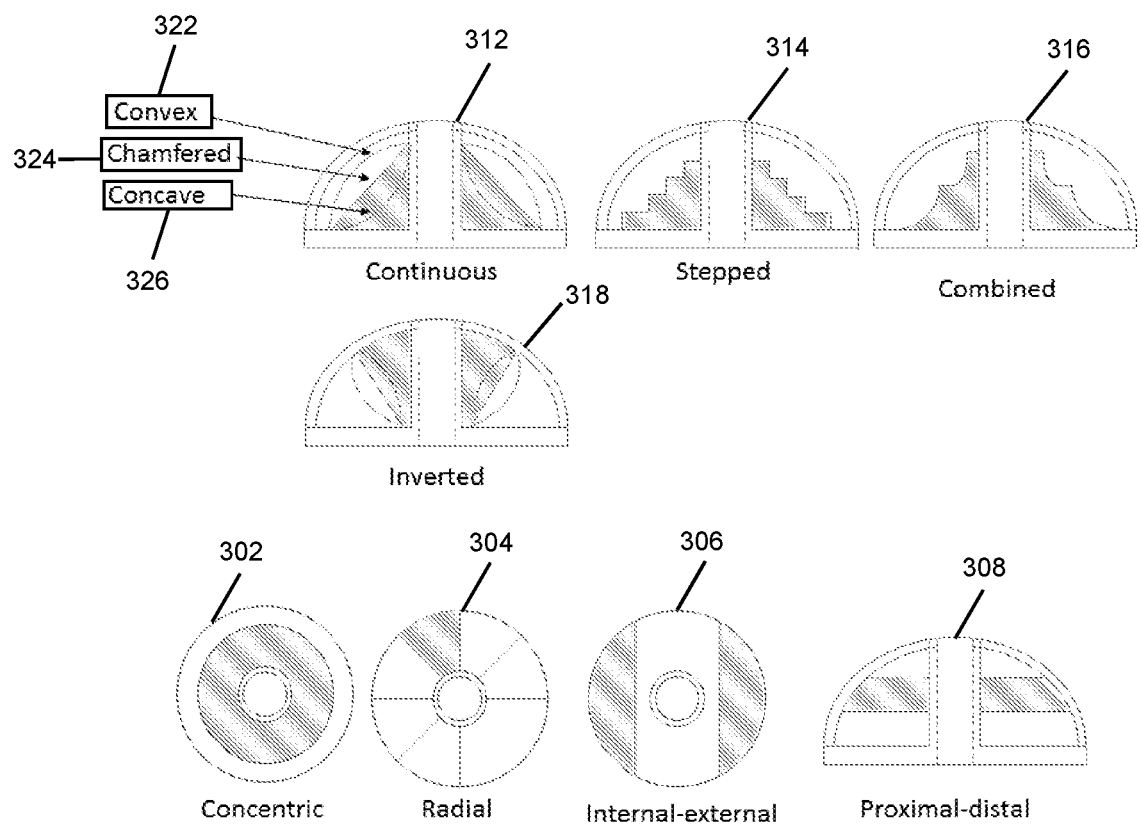
FIG. 3 illustrates various configurations of a perforated chamber ostomy wafer where white area represents viscous media placement and gray area represents structure.

Generally, the external layer (e.g., the external layer 210) and the convex layer (e.g., the convex layer 220) are layered or nested such that the stoma channel (e.g., the stoma channel 260) is positioned within the interior of the convex layer as suggested in FIG. 2. The convex layer may include multiple layers arranged in one of a number of layer arrangements. By way of non-limiting example, as shown in FIG. 3, the layer arrangements include a concentric arrangement 302, a radial arrangement 304, an internal-external arrangement 306, and a proximal-distal arrangement 308. Additionally, the convex layer may include structure(s) that provide one of a number of profiles and impart support and/or rigidity to the convex layer as a whole, or to one of more chambers of the convex layer. By way of non-limiting example, the profiles include a continuous profile 312, a stepped profile 314, a combined profile 316, and an inverted profile 318. Furthermore, each of the profiles may include various aspects or features. By way of non-limiting example, each of the profiles may include convex aspect or features 322, concave aspects or features 324, chamfered aspects or features 326, or combinations thereof.

The chamber of the convex layer (e.g., the chamber 340) may be centrally or eccentrically placed relative to the stoma aperture (e.g., the stoma channel 360). The chamber may have a proximal chamber opening (e.g., the opening 362) that is positioned within the interior of the convex layer. Prior to use, the chamber may occupy between 20 and 90% of the total volume of the ostomy wafer, at least in some embodiments. Upon use, the chamber may occupy between 40 and 90% of the total volume of the ostomy wafer, at least in some embodiments.

The ostomy wafer may include an internal layer that at least partially covers the convex surface of the convex layer and has an adhesive on a stoma-facing side thereof for attachment to the peristomal skin (which may adhere the internal layer to flush/retracted skin of the flush/retracted stoma and secure the ostomy wafer to the ostomate). The internal layer may include one or more perforations for passage of the viscous media therethrough and on to the peristomal skin.

Perforations

The ostomy wafers of the present disclosure include at least one perforation (e.g., the perforations 170) as indicated above. Generally, the convex layer and/or the internal layer include one or more perforations sized appropriately for the dimensions of the ostomy wafer. In one example, one or more of the perforations may range from about 0.5 mm to about 10 mm in diameter. In another example, one or more of the perforations may range from about 0.5 mm to about 5 mm in diameter. In yet another example, one or more of the perforations may range from about 1 mm to about 5 mm in diameter.

It should be appreciated that the dimensions of the perforations should be appropriate for the viscous media to seep out from, or be extruded from, the ostomy wafer such that the viscous media reaches the peristomal skin. By way of non-limiting example, the width or diameter of the perforations may range from less than a millimeter to as great as one centimeter, at least in some embodiments. In some cases, the perforations may be numerous, but microscopic in size. In other cases, the perforations may be few, but on a centimeter scale. The spacing of the perforations from one another can range from less than a millimeter to two centimeters. The non-perforated area between perforations may cover up to 90% of an area of the external layer, the convex layer, and/or the internal layer. The perforations may be sized and spaced from one another to ensure a relatively even distribution of the viscous media to the abdomen when an ostomy wafer is applied thereto. The perforations may be arranged in a number of patterns, such as a vertical pattern, a horizontal pattern, an oblique pattern, a spiral pattern, a staggered pattern, or an irregular pattern, for example.

The perforations may be distributed evenly throughout the convex layer and/or internal layer, at least in some embodiments. Additionally, in some embodiments, the perforations may be distributed and/or concentrated in a portion of the convex layer and/or the internal layer. By way of non-limiting example, the perforations may be distributed in a portion of the convex layer and/or the internal layer that is closest to the external layer. In some cases, it may be undesirable to contact internal tissue with viscous media. Rather, it may be preferable to contact only peristomal skin or predominantly peristomal skin with the viscous media, at least in some cases. Therefore, the perforations may be distributed in a region or portion of the convex layer and/or internal layer that is closest to the external layer.

In some embodiments, the perforations may be distributed over at least about 90% of the convex layer and/or the internal layer that is closest to the external layer. Additionally, in some embodiments, the perforations may be distributed over at least about 80% of the convex layer and/or the internal layer that is closest to the external layer. In some embodiments still, the perforations may be distributed over at least about 70% of the convex layer and/or the internal layer that is closest to the external layer. In some embodiments yet still, the perforations may be distributed over at least about 60% of the convex layer and/or the internal layer that is closest to the external layer.

In some embodiments, the perforations may be distributed over at least about 50% of the convex layer and/or the internal layer that is closest to the external layer. In some embodiments still, the perforations may be distributed over at least about 40% of the convex layer and/or the internal layer that is closest to the external layer. In some embodiments yet still, the perforations may be distributed over at least about 30% of the convex layer and/or the internal layer that is closest to the external layer. Further, the perforations may be distributed over at least about 20% of the convex layer and/or the internal layer that is closest to the external layer, at least in some embodiments. Finally, in some embodiments, the perforations may be distributed over at least about 10% of the convex layer and/or the internal layer that is closest to the external layer.

In some embodiments, the majority of the perforations may be distributed in the portion of the convex layer and/or the internal layer that is closest to the external layer. In one example, at least about 20% of the perforations may be distributed over at least about 90% of the convex layer and/or the internal layer that is closest to the external layer. In another example, at least about 20% of the perforations may be distributed over at least about 80% of the convex layer and/or the internal layer that is closest to the external layer. In yet another example, at least about 20% of the perforations may be distributed over at least about 70% of the convex layer and/or the internal layer that is closest to the external layer. In yet another example still, at least about 20% of the perforations may be distributed over at least about 60% of the convex layer and/or the internal layer that is closest to the external layer.

In some embodiments, at least about 20% of the perforations may be distributed over at least about 50% of the convex layer and/or the internal layer that is closest to the external layer. Additionally, in some embodiments, at least about 20% of the perforations may be distributed over at least about 40% of the convex layer and/or the internal layer that is closest to the external layer. In some embodiments still, at least about 20% of the perforations may be distributed over at least about 30% of the convex layer and/or the internal layer that is closest to the external layer. Further, in some embodiments, at least about 20% of the perforations may be distributed over at least about 20% of the convex layer and/or the internal layer that is closest to the external layer. Finally, in some embodiments, at least about 20% of the perforations may be distributed over at least about 10% of the convex layer and/or the internal layer that is closest to the external layer.

In some embodiments, the majority of the perforations may be distributed in the portion of the convex layer and/or the internal layer that is closest to the external layer. In one example, at least about 30% of the perforations may be distributed over at least about 90% of the convex layer and/or the internal layer that is closest to the external layer. In another example, at least about 30% of the perforations may be distributed over at least about 80% of the convex layer and/or the internal layer that is closest to the external layer. In yet another example still, at least about 30% of the perforations may be distributed over at least about 70% of the convex layer and/or the internal layer that is closest to the external layer. Finally, in some embodiments, at least about 30% of the perforations may be distributed over at least about 60% of the convex layer and/or the internal layer that is closest to the external layer.

In some embodiments, at least about 30% of the perforations may be distributed over at least about 50% of the convex layer and/or the internal layer that is closest to the external layer. Additionally, in some embodiments, at least about 30% of the perforations may be distributed over at least about 40% of the convex layer and/or the internal layer that is closest to the external layer. In some embodiments still, at least about 30% of the perforations may be distributed over at least about 30% of the convex layer and/or the internal layer that is closest to the external layer. In some embodiments yet still, at least about 30% of the perforations may be distributed over at least about 20% of the convex layer and/or the internal layer that is closest to the external layer. Finally, in some embodiments, at least about 30% of the perforations may be distributed over at least about 10% of the convex layer and/or the internal layer that is closest to the external layer.

In some embodiments, the majority of the perforations may be distributed in the portion of the convex layer and/or the internal layer that is closest to the external layer. In one example, at least about 40% of the perforations may be distributed over at least about 90% of the convex layer and/or the internal layer that is closest to the external layer. In another example, at least about 30% of the perforations may be distributed over at least about 80% of the convex layer and/or the internal layer that is closest to the external layer. In yet another example, at least about 40% of the perforations may be distributed over at least about 70% of the convex layer and/or the internal layer that is closest to the external layer. In yet another example still, at least about 40% of the perforations may be distributed over at least about 60% of the convex layer and/or the internal layer that is closest to the external layer.

In some embodiments, at least about 30% of the perforations may be distributed over at least about 50% of the convex layer and/or the internal layer that is closest to the external layer. Additionally, in some embodiments, at least about 30% of the perforations may be distributed over at least about 40% of the convex layer and/or internal layer that is closest to the external layer. In some embodiments still, at least about 40% of the perforations may be distributed over at least about 30% of the convex layer and/or the internal layer that is closest to the external layer. In some embodiments yet still, at least about 40% of the perforations may be distributed over at least about 20% of the convex layer and/or the internal layer that is closest to the external layer. Finally, in some embodiments, at least about 40% of the perforations may be distributed over at least about 10% of the convex layer and/or the internal layer that is closest to the external layer.

In some embodiments, the majority of the perforations may be distributed in the portion of the convex layer and/or the internal layer that is closest to the external layer. In one example, at least about 50% of the perforations may be distributed over at least about 90% of the convex layer and/or the internal layer that is closest to the external layer. In another example, at least about 30% of the perforations may be distributed over at least about 80% of the convex layer and/or the internal layer that is closest to the external layer. In yet another example, at least about 50% of the perforations may be distributed over at least about 70% of the convex layer and/or the internal layer that is closest to the external layer. In yet another example still, at least about 50% of the perforations may be distributed over at least about 60% of the convex layer and/or the internal layer that is closest to the external layer.

In some embodiments, at least about 50% of the perforations may be distributed over at least about 50% of the convex layer and/or the internal layer that is closest to the external layer. Additionally, in some embodiments, at least about 50% of the perforations may be distributed over at least about 40% of the convex layer and/or the internal layer that is closest to the external layer. In some embodiments still, at least about 50% of the perforations may be distributed over at least about 20% of the convex layer and/or the internal layer that is closest to the external layer. In some embodiments yet still, at least about 50% of the perforations may be distributed over at least about 10% of the convex layer and/or the internal layer that is closest to the external layer.

In some embodiments, the majority of the perforations may be distributed in the portion of the convex layer and/or the internal layer that is closest to the external layer. In one example, at least about 60% of the perforations may be distributed over at least about 90% of the convex layer and/or the internal layer that is closest to the external layer. In another example, at least about 30% of the perforations may be distributed over at least about 80% of the convex layer and/or the internal layer that is closest to the external layer. In yet another example, at least about 60% of the perforations may be distributed over at least about 70% of the convex layer and/or the internal layer that is closest to the external layer. In yet another example still, at least about 60% of the perforations may be distributed over at least about 60% of the convex layer and/or the internal layer that is closest to the external layer.

In some embodiments, at least about 60% of the perforations may be distributed over at least about 50% of the convex layer and/or the internal layer that is closest to the external layer. Additionally, in some embodiments, at least about 60% of the perforations may be distributed over at least about 40% of the convex layer and/or the internal layer that is closest to the external layer. In some embodiments still, at least about 60% of the perforations may be distributed over at least about 30% of the convex layer and/or the internal layer that is closest to the external layer. In some embodiments yet still, at least about 60% of the perforations may be distributed over at least about 20% of the convex layer and/or the internal layer that is closest to the external layer. Finally, in some embodiments, at least about 60% of the perforations may be distributed over at least about 10% of the convex layer and/or the internal layer that is closest to the external layer.

In some embodiments, the majority of the perforations may be distributed in the portion of the convex layer and/or the internal layer that is closest to the external layer. In one example, at least about 70% of the perforations may be distributed over at least about 90% of the convex layer and/or the internal layer that is closest to the external layer. In another example, at least about 70% of the perforations may be distributed over at least about 80% of the convex layer and/or the internal layer that is closest to the external layer. In yet another example, at least about 70% of the perforations may be distributed over at least about 70% of the convex layer and/or the internal layer that is closest to the external layer. In yet another example still, at least about 70% of the perforations may be distributed over at least about 60% of the convex layer and/or the internal layer that is closest to the external layer.

In some embodiments, at least about 70% of the perforations may be distributed over at least about 50% of the convex layer and/or the internal layer that is closest to the external layer. Additionally, in some embodiment, at least about 70% of the perforations may be distributed over at least about 40% of the convex layer and/or the internal layer that is closest to the external layer. In some embodiments still, at least about 70% of the perforations may be distributed over at least about 30% of the convex layer and/or the internal layer that is closest to the external layer. In some embodiments yet still, at least about 70% of the perforations may be distributed over at least about 20% of the convex layer and/or the internal layer that is closest to the external layer. Finally, in some embodiments, at least about 70% of the perforations may be distributed over at least about 10% of the convex layer and/or the internal layer that is closest to the external layer.

In some embodiments, the majority of the perforations may be distributed in the portion of the convex layer and/or the internal layer that is closest to the external layer. In one example, at least about 80% of the perforations may be distributed over at least about 90% of the convex layer and/or the internal layer that is closest to the external layer. In another example, at least about 80% of the perforations may be distributed over at least about 80% of the convex layer and/or the internal layer that is closest to the external layer. In yet another example, at least about 80% of the perforations may be distributed over at least about 70% of the convex layer and/or the internal layer that is closest to the external layer. In yet another example still, at least about 80% of the perforations may be distributed over at least about 60% of the convex layer and/or the internal layer that is closest to the external layer.

In some embodiments, at least about 80% of the perforations may be distributed over at least about 50% of the convex layer and/or the internal layer that is closest to the external layer. Additionally, in some embodiments, at least about 80% of the perforations may be distributed over at least about 40% of the convex layer and/or the internal layer that is closest to the external layer. In some embodiments still, at least about 80% of the perforations may be distributed over at least about 30% of the convex layer and/or the internal layer that is closest to the external layer. In some embodiments yet still, at least about 80% of the perforations may be distributed over at least about 20% of the convex layer and/or the internal layer that is closest to the external layer. Finally, in some embodiments, at least about 80% of the perforations may be distributed over at least about 10% of the convex layer and/or the internal layer that is closest to the external layer.

In some embodiments, the majority of the perforations may be distributed in the portion of the convex layer and/or the internal layer that is closest to the external layer. In one example, at least about 90% of the perforations may be distributed over at least about 90% of the convex layer and/or the internal layer that is closest to the external layer. In another example, at least about 90% of the perforations may be distributed over at least about 80% of the convex layer and/or the internal layer that is closest to the external layer. In yet another example, at least about 90% of the perforations may be distributed over at least about 70% of the convex layer and/or the internal layer that is closest to the external layer. In yet another example still, at least about 90% of the perforations may be distributed over at least about 60% of the convex layer and/or the internal layer that is closest to the external layer.

In some embodiments, at least about 90% of the perforations may be distributed over at least about 50% of the convex layer and/or the internal layer that is closest to the external layer. Additionally, in some embodiments, at least about 90% of the perforations may be distributed over at least about 40% of the convex layer and/or the internal layer that is closest to the external layer. In some embodiments still, at least about 90% of the perforations may be distributed over at least about 30% of the convex layer and/or the internal layer that is closest to the external layer. In some embodiments yet still, at least about 90% of the perforations may be distributed over at least about 20% of the convex layer and/or the internal layer that is closest to the external layer. Finally, in some embodiments, at least about 90% of the perforations may be distributed over at least about 10% of the convex layer and/or the internal layer that is closest to the external layer.

In some embodiments, the perforations may be circular, oblong, rectangular, square, polygonal, triangular, octagonal, hexagonal, or irregular-shaped. In other embodiments, the perforations may take the shape of another suitable geometric form. The perforations may be slits or cracks, at least in some embodiments. The ostomy wafer, or any portion thereof with the perforations, may resemble a sieve, net, grid, filter, sponge, or the like, at least in some embodiments.

In some embodiments, the sizes of the perforations may vary at different locations on the wafers. By way of non-limiting example, perforations on the convex layer may be larger near the proximal opening (e.g., the opening 162) than perforations on the convex layer near the distal opening (e.g., the opening 164). In other embodiments, however, perforations on the convex layer may be smaller near the proximal opening than perforations on the convex layer near the distal opening. The perforations may have an average range from about 10 mm to about 100 mm in diameter, at least in some embodiments. Additionally, in some embodiments, the perforations may have an average range from about 20 mm to about 50 mm in diameter.

Chambers

The ostomy wafers of the present disclosure may include a single chamber or multiple chambers. In one example, the ostomy wafer may include one chamber. In another example, the ostomy wafer may include two chambers. In yet another example, the ostomy wafer may include three chambers. In yet another example still, the ostomy wafer may include four chambers. Further, in some embodiments, the ostomy wafer may include five chambers. In some embodiments still, the ostomy wafer may include six chambers. In some embodiments yet still, the ostomy wafer may include seven chambers. The ostomy wafer may include eight chambers, at least in some embodiments. Further, in some embodiments, the ostomy wafer may include nine chambers. Additionally, the ostomy wafer may include ten chambers, at least in some embodiments. Finally, in some embodiments, the ostomy wafer may include twelve chambers.

In some embodiments, the ostomy wafer disclosed herein may include from one chamber to about twenty chambers. In one example, the ostomy wafer may include from two chambers to about twenty chambers. In another example, the ostomy wafer may include from three chambers to about twenty chambers. In yet another example still, the ostomy wafer may include from four chambers to about twenty chambers. Finally, in another example, the ostomy wafer may include from five chambers to about twenty chambers.

The ostomy wafers of the present disclosure may include one or more chambers in which one or more dividers, walls, ridges, grooves, sections, or any other space defining features are arranged. In some embodiments, the ostomy wafer may include a first chamber and a second chamber that are arranged side-by-side as they encircle an opening of any one of the layers, or as they radiate from an opening of any one of the layers. Additionally, in some embodiments, the first chamber and the second chamber may be concentrically arranged as they radiate from an opening of any one of the layers.

Multiple chambers of the ostomy wafers of the present disclosure may allow for viscous media to be present in a first portion of the convex layer and not present in a second portion of the convex layer, at least in some embodiments. In other embodiments, multiple chambers may allow for viscous media to be present in a first amount in a first portion of the convex layer and present in a second amount in a second portion of the convex layer. In one example, the first portion may be about 10% of the convex layer. In another example, the first portion may be about 20% of the convex layer. In yet another example, the first portion may be about 30% of the convex layer. In yet another example still, the first portion may be about 40% of the convex layer. Further, in another example, the first portion may be about 50% of the convex layer. Further, in yet another example, the first portion may be about 60% of the convex layer. Further, in yet another example still, the first portion may be about 70% of the convex layer. The first portion may be about 80% of the convex layer, at least in some embodiments. Finally, in some embodiments, the first portion may be about 90% of the convex layer.

In some embodiments, the aforementioned second portion may be about 10% of the convex layer of any ostomy wafer disclosed herein. Additionally, in some embodiments, the second portion may be about 20% of the convex layer. In some embodiments still, the second portion may be about 30% of the convex layer. In some embodiments yet still, the second portion may be about 40% of the convex layer. Further, in some embodiments, the second portion may be about 50% of the convex layer. Further, in some embodiments still, the second portion may be about 60% of the convex layer. Further, in some embodiments yet still, the second portion may be about 70% of the convex layer. The second portion may be about 80% of the convex layer, at least in some embodiments. Finally, in some embodiments, the second portion may be about 90% of the convex layer.

In some embodiments, the aforementioned first amount may be about 10% of the convex layer of any ostomy wafer of the present disclosure. Additionally, in some embodiments, the first amount may be about 20% of the convex layer. In some embodiments still, the first amount may be about 30% of the convex layer. In some embodiments yet still, the first amount may be about 40% of the convex layer. Further, in some embodiments, the first amount may be about 50% of the convex layer. Further, in some embodiments still, the first amount may be about 60% of the convex layer. Further, in some embodiments yet still, the first amount may be about 70% of the convex layer. The first amount may be about 80% of the convex layer, at least in some embodiments. Finally, in some embodiments, the first amount may be about 90% of the convex layer.

The previously mentioned second amount may be about 10% of the convex layer of any ostomy wafer disclosed herein, at least in one example. In another example, the second amount may be about 20% of the convex layer. In yet another example, the second amount may be about 30% of the convex layer. In yet another example still, the second amount may be about 40% of the convex layer. Further, in another example, the second amount may be about 50% of the convex layer. Further, in yet another example, the second amount may be about 60% of the convex layer. Further, in yet another example still, the second amount may be about 70% of the convex layer. The second amount may be about 80% of the convex layer, at least in one example. Finally, in another example, the second amount may be about 90% of the convex layer.

In some embodiments, the ostomy wafers of the present disclosure may include multiple chambers arranged such that two chambers containing viscous media are separated by at least one chamber not containing viscous media. Additionally, in some embodiments, two chambers containing viscous media are continuous or consecutive. It should be appreciated that multiple chambers may facilitate application of viscous media (e.g., by the user or ostomate) in select regions around the device and/or stoma of the user.

In some embodiments, the volume of viscous media in the chamber may range up to 95% of the total ostomy wafer volume. Additionally, in some embodiments, chamber size may vary with ostomy wafer size, and convexity may range from 5% of total volume up to 90% of total ostomy wafer volume. In some embodiments still, chamber size may range from about 15% of total volume up to 95% of total ostomy wafer volume. In some embodiments yet still, chamber size may range from about 20% of total volume up to 95% of total ostomy wafer volume. Further, in some embodiments, chamber size may range from about 25% of total volume up to 95% of total ostomy wafer volume. Further, in some embodiments still, chamber size may range from about 30% of total volume up to 95% of total ostomy wafer volume. Finally, in some embodiments, chamber size may range from about 35% of total volume up to 95% of total ostomy wafer volume.

Figure 4A:
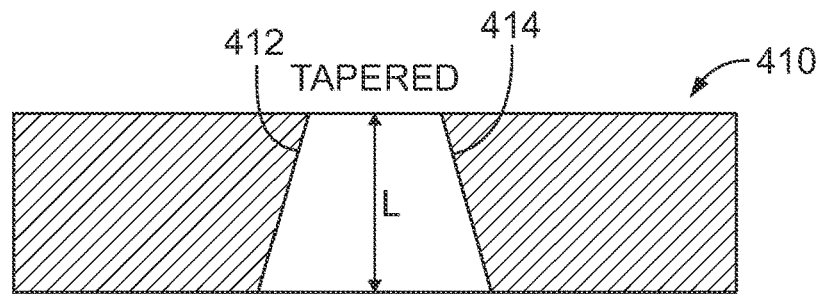
FIG. 4A illustrates a side view of a number of structures that may define, or be located in close proximity to, a stoma channel formed in a perforated chamber ostomy wafer.
Figure 4A:
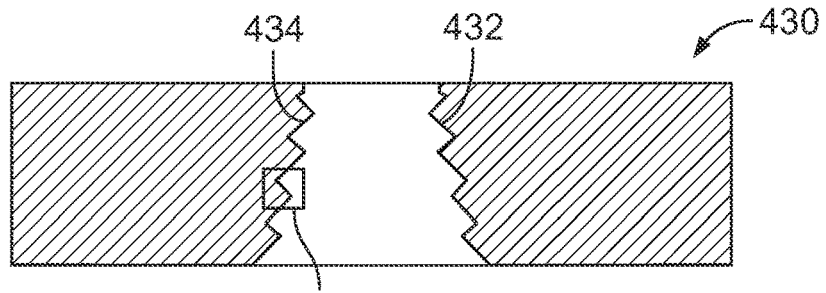
Figure 4A:
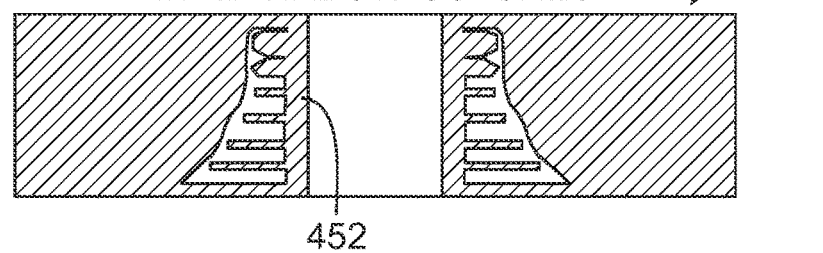
Figure 4B:
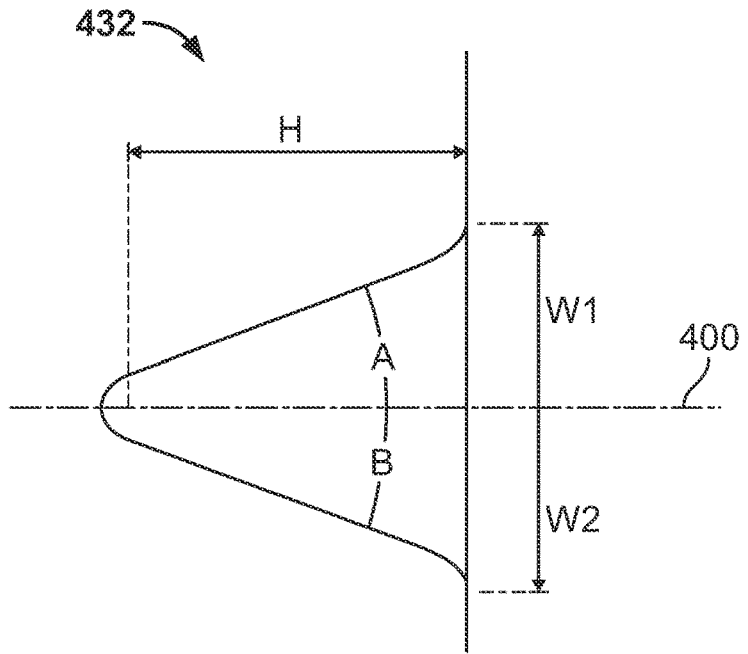
FIG. 4B illustrates a magnified view of one of the structures illustrated in FIG. 4A.

In some embodiments, the ostomy wafers disclosed herein may include features to control deformation thereof in use. The features may include, but are not limited to, struts, fins, walls, columns, and combinations thereof (e.g., in the order of 0.1 mm to 10 mm in their greatest dimension). In one example, the ostomy wafer may include structures 410 shown in FIG. 4A that are embodied as, or otherwise include, angled and/or tapered surfaces 412, 414. In some embodiments, the surfaces 412, 414 may define, or otherwise incorporate, one or more angled fins 432 defining notches 434 therebetween, which are depicted in FIG. 4A and which may be embodied as, or otherwise included in, the structures 430. In any case, in some embodiments, each angled fin 432 and/or each notch 434 may have a height H (shown in FIG. 4B) of about 0.01 mm to about 10 mm. The height H may be the dimension perpendicular to a length L of the stoma channel (e.g., the stoma channel 160). As shown in FIG. 4B, each angled fin 432 may have a width W1 measured with respect to a horizontal line 440 that is from 0.01 mm to 10 mm and a width W2 measured with respect to the line 440 that is from 0.01 mm to 20 mm. Additionally, as shown in FIG. 4B, each angled fin 432 may extend at an angle A relative to the line 440 that is from 0° to 60° and at an angle B relative to the line 440 that is from and angle B is 0-90°.

In some embodiments, ostomy wafers disclosed herein may include structures (e.g., the structures 430) located on the inner wall(s) defining the stoma channel that facilitate controlled deformation of the ostomy wafer in use thereof. Additionally, in some embodiments, the structures disclosed located on the inner surface of the stoma channel are tapered (e.g., the structures 410) or jagged (e.g., the structures 430), which may prevent or resist detachment of the ostomy wafer from the protruding stoma, at least in some embodiments. In some embodiments still, the structures disclosed herein provide internal structures (e.g., the structures 450 within the stoma channel wall(s) 452) that provide deformation and malleability without gripping and/or directly contacting the stoma.

In some embodiments, the ostomy wafers of the present disclosure may include a structural support to achieve optimum convexity upon dispersal of the viscous media. Additionally, in some embodiments, the structural support may produce greater stomal protrusion and provide enhanced protection for recessed, retracted, or flush stomas. Structural supports may include one or more of various materials. By way of non-limiting example, those materials may include rigid or semi-rigid plastics such as polypropylene, polystyrene, or polyethylene (e.g., polyethylene-vinyl acetate), at least in some embodiments.

In similar fashion to the arrangements of the multiple layers of the convex layer described above with reference to FIG. 3, a plurality of support structures may be arranged radially, concentrically, in proximal-distal layers, or in internal-external layer, at least in some embodiments. The support structures may be present at a macro level (with dimensions of several mm) and at a micro level (in the order of μm). Additionally, in some embodiments, the support structures may function to control gross structural deformation to within about 80% of original ostomy wafer volume. In some embodiments still, the surface profile of the ostomy wafer may contain features to guide movement of, and/or control distribution of, viscous media, such as corrugated peaks and troughs in regular or irregular patterns, for example. Those features may vary in height from 10 μm to 10 mm. Furthermore, the ostomy wafer may have surface texture with a surface roughness Ra (μm) ranging from 0.01 to 50.

Deformation characteristics of the ostomy wafers disclosed herein may be anisotropic, at least in some embodiments. In most cases, however, that deformation is below about 30 mm and about 90% of total ostomy wafer volume. Adhesive components may fill structural voids having a minimum volume of about 1 mm³, at least in some embodiments. Additionally, in some embodiments, adhesive components may fill structural voids having a minimum size of about 0.1 mm³. In some embodiments, adhesive components may fill structural voids having a minimum size of about 0.01 mm³.

Adhesives

The illustrative, three-dimensional, moldable ostomy wafers of the present disclosure generally include adhesives or adhesive layers. As used herein, the term "adhesive" refers to layers, fabrics, strips, laminates, barriers, gels, pastes, hydrocolloids, glues, or the like that may be used to promote adherence of the ostomy wafer to the ostomate and/or promote a seal between the ostomy wafer and the ostomate to resist undesirable leakage of effluent.

The adhesives disclosed herein may be substantially liquid impermeable and may permeate moisture away from the skin, at least in some embodiments. The adhesives may have a moisture vapor transmission rate (MVTR) greater than 50 g/m²/24 h, greater than 100 g/m²/24 h, or greater than 150 g/m²/24 h. Additionally, in some embodiments, the adhesives may have a MVTR greater than 200 g/m²/24 h.

In some embodiments, the adhesives may include a polymer selected from, but not limited to, polypropyleneoxide, polyurethane, silicone, polyacrylate, ethylene vinyl acetate and combinations thereof. Additionally, in some embodiments, the adhesive may include a hydrocolloid. The adhesive may be at least 1%, at least 5%, at least 10%, at least 15%, at least 20%, or at least 30% w/v hydrocolloid, but less than 70% w/v hydrocolloid, at least in some embodiments. In some embodiments still, the adhesive may include a salt. In such embodiments, the salt may be selected from sodium chloride, calcium chloride, potassium sulfate, sodium bicarbonate, disodium carbonate, potassium chloride, sodium bromide, sodium iodide, potassium iodide, ammonium chloride, and aluminum chloride.

The adhesive may include a sealing substance that promotes a seal between the ostomy wafer and the stoma/ostomate, at least in some embodiments. It should be appreciated, however, that in some embodiments, inclusion of an adhesive in the ostomy wafer may be unnecessary. In some embodiments, kits and/or methods contemplated by the present disclosure may include an adhesive or involve the use of an adhesive, and the adhesive (e.g., an adhesive paste) may be applied to the ostomy wafer to effectively eliminate gaps between the stoma and the ostomy wafer in use of the ostomy wafer.

Adhesives may also be used to promote adherence of an ostomy pouch to the ostomy wafer. The adhesives disclosed herein may provide adhesion for a variety of skin conditions, as well as security and comfort for the patient. In some embodiments, to ensure the skin barrier adheres to moist/dry skin, hydrocolloids may be used. Additionally, in some embodiments, the adhesives, such as barriers, seals, strips, laminates, or fabrics, for example, may include a release liner designed for removal prior to use. In other embodiments, however, the adhesives may not include a release liner. In such embodiments, the adhesive quality of the adhesive may be present only when the adhesive makes contact with a liquid, gel, effluent, skin, heat, or a combination thereof. Furthermore, in some embodiments, the adhesives may have an adhering, sealing, or molding quality that is activated and/or promoted by heat and/or contact with effluent.

Adhesives disclosed herein may include a component or material selected from, but not limited to, chitosan, pectin, gelatin, carboxymethylcellulose, a butadiene polymer, a poly-α-olefin, an absorbent microcolloid particle, a cross-linked hydrophilic polymer, a p-toluene-suffonamide, a polymeric matrix, a thermoplastic elastomer, a polyolefin elastomer, a copolymer of ethylene and octane, a silicone elastomer, carboxymethyl cellulose, an acrylate, an alginate, a polysaccharide, a homopolymer, a block co-polymer, a hydrogel-forming hydrophilic homopolymer, a heteropolymer, an amphiphilic block-copolymer, a cross-linked polyalkyleneoxide polymer, a triblock copolymer, a plasticising oil (e.g., liquid rosin derivative, aromatic olefin oligomer, vegetable or animal oil, ester, ether, glycol, poly propylene oxide, alpha-butoxy-polyoxypropylene), a polar polyethylene copolymer, a polypropyleneoxide, a polar polyethylene copolymer, ethylene vinyl acetate, ethylene vinyl acetate carbon monoxide, ethylene butyl acetate, ethylene vinyl alcohol, ethylene butyl acrylate, ethylene butyl acrylate monoxide, a styrene-isoprene-styrene copolymer, a tackifier, paraffin oil, a hydrocolloid, a mono-oligosaccharide, a di-oligosaccharide, a sugar alcohol, a polypeptide, an organic acid, an inorganic acid, an amino acid, an amine, urea, and a glycol, and combinations thereof.

In an exemplary embodiment, the ostomy wafers disclosed herein may include ConvaTec Moldable adhesive Technology (CMT), which improves the fit between skin barriers and stomas. In one example, Durahesive™ technology used in CMT may help to protect the skin from caustic effluent. Durahesive™ technology combines the ingredients used in Stomahesive™ technology in a different ratio to produce a moisture-absorbing adhesive. In some embodiments, the inclusion of Durahesive™ technology in convex wafers may ensure easy one-piece removal (i.e., due to higher cohesive strength) that is gentle on the surrounding skin. Durahesive™ polymers may swell within an elastic matrix to create a seal around the stoma site. Durahesive™ polymers may swell or "turtleneck" in response to coming in contact with liquid effluent to improve the seal around the stoma. The expansion and contraction around the stoma in use of such polymers may provide a barrier that remains snug and secure during period of wear. It should be appreciated that ensuring a good seal around the stoma minimizes the risk of effluent leaking under the skin barrier, and that reducing such leakage resists the development of peristomal skin complications.

In an exemplary embodiment, the ostomy wafers disclosed herein may include ConvaTec Moldable adhesive Technology (CMT), which improves the fit between skin barriers and stomas. In one example, Durahesive™ technology used in CMT may help to protect the skin from caustic effluent. Durahesive™ polymers may swell within an elastic matrix to create a seal around the stoma site. Durahesive™ polymers may swell or "turtleneck" in response to coming in contact with liquid effluent to improve the seal around the stoma. The expansion and contraction around the stoma in use of such polymers may provide a barrier that remains snug and secure during period of wear. It should be appreciated that ensuring a good seal around the stoma minimizes the risk of effluent leaking under the skin barrier, and that reducing such leakage resists the development of peristomal skin complications.

In some embodiments, the ostomy wafers disclosed herein and components thereof may include a hydrocolloid adhesive, such as Pectin, Gelatin, and NaCMC (Sodium Carboxymethyl Cellulose), for example. The term "hydrocolloid adhesive" as used herein refers to an adhesive material or substance that includes a hydrocolloid. Exemplary embodiments of hydrocolloid adhesives include, but are not limited to, Stomahesive™ Durahesive™, Trilaminate, and Stomahesive™ Seal. The formulation of those adhesives may be altered to increase further the product's appeal (e.g. comfort, flexibility, size, breathability, etc.). To improve the elasticity of the adhesive, an addition of a material (e.g., styrene-isoprene-styrene (SIS) rubber, isobutylene, etc.) may be added. Oils may also be added to enhance the pliability and tack. As used herein, any reference to "Trilam" generally refers to a trilaminate system. Furthermore, as used herein, any reference to "Trilam SH/DH" generally refers to a trilaminate system that incorporates a Stomahesive™ (SH) layer, a film layer, and a Durahesive™ (DH) layer. In some cases, the film layer may be embodied as, or otherwise include, a layer incorporating PET film.

The adhesives disclosed herein may include a mucoadhesive. The mucoadhesive may be particularly helpful to maintain sufficient adhesion under wet conditions, among other conditions. In some embodiments, the mucoadhesive of the present disclosure includes a polymer having functional groups selected to provide adhesion to the skin and the stoma. In one example, the functional groups are selected from a group consisting of thiols, acids and their salts, iminothiolanes, thioalkylamidines, catechols, amino acids, dihydroxy substituted aromatic groups, and combinations thereof. Additionally, in one example, the polymer is a biocompatible polymer made from natural or synthetic polymer selected from a group consisting of polyacrylates, polyakylmethacrylates, polyphenylmethacrylate, polyanhydrides, styrenic block copolymers, polyamides, polyesters, polyvinyl ethers, polyvinyl esters, sulfonated polymers, polyolefins, silicones, polyvinylpyrrolidones, polyvinylacetate and its copolymers, polyvinyl alcohol, polyurethanes, polyethers, copolymers of maleic anhydride, polysaccharides, polypeptides, gelatin, alginates, gums, starch, chitosan, pectin, and combinations thereof. Further, in some embodiments, the mucoadhesive may contain other components such as hydrophobic polymers, hydrophilic polymers, amphiphilic polymers, tackifiers, resins, plasticizers, hydrocolloids, inorganic and organic particulate fillers, antioxidants, stabilisers, organic and inorganic pigments, lubricious additives, and combinations thereof.

The adhesives may include a pressure sensitive adhesive having one or more amphiphilic copolymers of polydimethylsiloxane, at least in some embodiments. In such embodiments, the copolymer may be prepared using a polydimethylsiloxane or polymethylhydrogensiloxane macroinitiator and at least one reactive hydrophilic or amphiphilic monomer, oligomer, macromere, or combinations thereof. In some embodiments, the reactive hydrophilic or amphiphilic monomer may be selected from a group consisting of N-vinyl caprolactams, vinyl esters, vinyl ethers, unsaturated acids or anhydrides and their salts, acrylates, methacrylates, acrylamides, methacrylamides, N-alkyl acrylamides, cyanate esters, hydroxy-alkyl acrylamides, glycidyl esters, glycidyl ethers, allyl monomers, and combinations thereof.

Viscous Media

Viscous media (e.g., viscous media 150) may also be referred to as one or more viscous solutions. Viscous media may be sticky or adhesive to promote adherence and establish a seal between the wafer and the ostomate, at least in some embodiments. Viscous media may include a paste and/or gel. Non-limiting examples of pastes include ConvaTec's Stomahesive™ paste, Adapt Paste (Hollister), Brava Paste (Coloplast), Securiti-T Stoma Paste (Genairex), MicroHesive Stoma Paste (Cymed), and Osto Stoma Paste (Montreal Osto). Gels include, but are not limited to, Silicone Gel (Trio), and Osto Paste (Stoma-Tech). Additionally, in some embodiments, ingredients of the pastes/gels may include, but are not limited to, Sodium Carboxymethylcellulose, Thixcin, Gelatin, and Pectin.

Viscous media, as contemplated herein, may have a viscosity of about 0.1 Pa·s$^{-1}$ to about 150 Pa·s$^{-1}$ at room temperature (~25° C.), at least in some embodiments. Additionally, in some embodiments, the viscous media may have a viscosity of about 1 to about 100 Pa·s$^{-1}$ at room temperature. In some embodiments still, the viscous media may have a viscosity of about 5 to about 50 Pa·s$^{-1}$ at room temperature. In some embodiments yet still, the viscous media may have a viscosity of about 1 to about 10 Pa·s$^1$ at room temperature. Further, in some embodiments, the viscous media may have a viscosity of about 10 to about 100 Pa·s$^1$ at room temperature. Finally, in some embodiments, the viscous media may have a viscosity of about 5 to about 10 Pa·s$^{-1}$ at room temperature.

The viscous media may have a honey-like viscosity, a nectar-like viscosity, or a molasses-like viscosity at room temperature, at least in some embodiments. Additionally, in some embodiments, the viscous media may have a viscosity similar to peanut butter, lard, ketchup, or toothpaste at room temperature. In some embodiments still, the viscous media may have a honey-like viscosity, a nectar-like viscosity, or a molasses-like viscosity at body temperature (~37° C.). Furthermore, it should be appreciated that in some embodiments, the viscous media may have a sufficiently high viscosity for the viscous media to be pushed/extruded through, seep through, or flow through perforations of the ostomy wafer. Further still, the viscous media may have a sufficiently low viscosity for the viscous media to be maintained at the site of use (e.g. stoma), subsequent to placement of the wafer/ostomy wafer. Of course, the viscosity of the viscous media may vary with temperature (e.g., room temperature to body temperature), shear stress, or manipulation of the viscous media. In some instances, movement of the wafer or the subject may provide additional adhesion.

In some embodiments, the viscous media may seep through the perforations, spread into skin depressions/contours, or otherwise resist effluent leakage. Additionally, as indicated above, the viscous media may be extruded through perforations of the ostomy wafers. In some embodiments still, to achieve optimum function, the ostomy wafer may incorporate a viscous media selected on the basis of any one of the following: dimensional stability, time dependent curing, temperature dependent curing, pH activation, light/UV activation, chemo-activation, and an oxidative property. In some embodiments yet still, the viscous media may be hydrophobic, hydrophilic or amphipathic.

Wafer Layers

The ostomy wafers disclosed herein generally include multiple layers. The layers may include, but are not limited to, molds, adhesives, seals, barriers, and laminates. In some embodiments, any one of the layers may include a foam. The foam may be an open cell foam, at least in some embodiments. It should be appreciated that solutions or fluids used with the ostomy wafers disclosed herein may seep through the open cell foam or may be extruded through the open cell foam.

The ostomy wafers disclosed herein include an external layer that may be flexible or moldable, at least in some embodiments. The external layer may allow a user of the ostomy wafer to depress the external layer into the convex layer or chamber, thereby decreasing the volume of the chamber and extruding the viscous media through the perforations, at least in some embodiments. In one example, the external layer may include a single layer. In another example, the external layer may include a multilayer or multi-laminate material or multiple layers of material. In yet another example, the external layer may include a hydrocolloid adhesive.

In some embodiments, the external layer may include a material selected from a hydrocolloid adhesive having pectin, gelatin, and sodium carboxymethyl cellulose (NaCMC). Exemplary embodiments include, but are not limited to, Stomahesive™ Durahesive™, Modified Stomahesive™, or Coloplasts Brava strips. Other materials that may be included in the external layer include silicone, acrylics, cyanoacrylate (such as Liquiband, for example), rubbers, foams, cellulose, polyurethanes, polyethylenes, polyvinyl chlorides, ethylenevinyl acetates, polypropylenes, polytetrafluorethylenes, and polyisobutylenes. The external layer may comprise Trilam (SH/DH) having a Stomahesive™ seal or a Durahesive™ seal, at least in some embodiments.

In some embodiments, the convex layer of any ostomy wafer disclosed herein may include a skin barrier. The skin barrier may include a ring formed from, or in the form of, a mold. The convex layer and/or the skin barrier may include an adhesive that is embodied as, or otherwise includes, a stoma adhesive. The stoma adhesive may provide a barrier or seal against effluent to ensure a single-directional flow through the opening of the convex layer (see the effluent flow arrows in FIGS. 1 and 2). In one embodiment, the skin barrier is a moldable adhesive that is breathable and/or moisture-absorbing. By way of non-limiting example, the skin barrier may be selected from Stomahesive™ Seal (ConvaTec), Brava Moldable adhesive Ring (Coloplast), Eakin Cohesive Seal (ConvaTec), Adapt Barrier Ring (Hollister), SecuPlast Mouldable Seal (Salts), and Siltac (Trio).

The skin barriers contemplated by the present disclosure are adapted to fill in and/or be received in cavities/folds in the intact skin around the stoma to protect the underlying skin from contact with bodily fluids. In some embodiments, the skin barriers may be made from pectin-based, hydrocolloid-type ingredients, mineral oils, plasticisers, tackifiers, and elastomers, with varying compositions.

In some embodiments, the convex layer of any ostomy wafer disclosed herein may be relatively cylindrical, funnel-shaped, and/or bowl-shaped, with a rim (e.g., the rims 116, 216, 516 shown in respective FIGS. 1, 2, and 5) that is in contact with the external layer. The profile of the convex layer may include both convex and concave forms, at least in some embodiments. Additionally, in some embodiments, the profile of the convex layer may be stepped or continuous, with increments of about 0.1 mm to about 10 mm, or about 1 mm to about 10 mm (see FIG. 3).

The opening of the convex layer through which effluent flows is generally positioned at/near the base of the bowl, opposite the mouth/rim. It should be appreciated that the convex layer should have appropriate dimensions for positioning into, around, or against a flush or retracted stoma. In one example, with regards to a flush stoma, the opening of the convex layer may be sized to fit around internal tissue such that the convex exterior rim of the "bowl" contacts the peristomal skin around the internal tissue and minimally extends beyond the surface of the skin surrounding the stoma. In the example of a retracted stoma, the convex layer may have a relatively shallow bowl depth and be wide enough to leave little or no space between the peristomal skin and the exterior rim and/or sides of the convex layer.

In some embodiments, the depth of the convex layer bowl may be between about half of a centimeter and about ten centimeters. Additionally, in some embodiments, the depth of the bowl may be between about one centimeter and about 5 centimeters. In some embodiments still, the gross diameter of the wafer may be between about 50 mm and about 300 mm, about 50 mm and about 200 mm, or about 50 mm and about 200 mm. In some embodiments yet still, the height of the ostomy wafer may be about 1 mm to about 50 mm. Further, in some embodiments, the height of the ostomy wafer may be about 3 mm to about 30 mm. Finally, in some embodiments, the height of the ostomy wafer may be about 5 mm to about 50 mm.

In some embodiments, the aperture (e.g., the proximal opening 162) of any ostomy wafer of the present disclosure may fit stomas ranging in average diameter from about 10 mm to about 80 mm. Additionally, in some embodiments, the ostomy wafer aperture may fit stomas ranging in average diameter from about 10 mm to about 100 mm. In some embodiments still, the ostomy wafer aperture may fit stomas ranging in average diameter from about 10 mm to about 50 mm. Further, in some embodiments, the width of the bowl may be between about two centimeters and about ten centimeters. It should be appreciated that the convex layer, as well as additional components of the ostomy wafers, may be manufactured by use of compression molds with heat treatment for adhesive molding.

In some embodiments, the convex layer of any ostomy wafer described herein may include a single layer. Additionally, in some embodiments, the convex layer may include a multilayer or multi-laminate material or multiple layers of material. In some embodiments still, the convex layer may include a hydrocolloid adhesive. In some embodiments yet still, the convex layer may include a material selected from Stomahesive™ seal.

The external layer and the convex layer of any ostomy wafer disclosed herein may completely or partially overlap, at least in some embodiments. In some cases, the external layer and the convex layer may have the same outer diameters. In other cases, the convex layer may have a greater outer diameter than that of the external layer. Additionally, in other cases, the external layer may have a greater outer diameter than that of the convex layer. In some embodiments, the external layer and the convex layer may have the same inner diameters. Additionally, in some embodiments, the convex layer may have a greater inner diameter than that of the external layer. In some embodiments still, the external layer may have a greater inner diameter than that of the convex layer.

The ostomy wafer may include an internal layer (e.g., the internal layer 130, 530) as indicated above. The internal layer may be positioned on the convex surface of the convex layer so that the internal layer contacts peristomal skin, as seen in FIG. 5. The internal layer may include a moldable adhesive barrier, at least in some embodiments. Additionally, in some embodiments, a moldable adhesive barrier may include an adhesive designed as an ostomy accessory to aid adherence of a pouch/dressing to the skin around a stoma, thereby protecting the skin from effluent while conforming to the stoma and/or surrounding skin. The moldable adhesive barrier may have a putty-like or rubberlike consistency, at least in some embodiments. Furthermore, in some embodiments, the internal layer may include a material selected from Eakin Cohesive Seal (ConvaTec), Adapt Barrier Rings (Hollister), SecuPlast Mouldable Seal (Salts), and Siltac (Trio). The internal layer may include Stomahesive™ seal and/or Stomahesive™ paste, at least in some embodiments.

The ostomy wafer may include one or more additional layers, at least in some embodiments. In some embodiments, the one or more additional layers may include adhesive. In other embodiments, the one or more additional layers may not include adhesive. In some embodiments still, the one or more additional layers may include a material selected from adhesive, laminate, foam, gel, rubber, fabric, plastic, and combinations thereof. It should be appreciated that the one or more additional layers may contribute to the flexibility or moldable character of the ostomy wafer, at least in some embodiments.

Stoma Channel

In some embodiments, the stoma channel (e.g., the stoma channel 160) of any ostomy wafer of the present disclosure may include at least one structure (e.g., any one or more of the features 410, 430, 450) to enhance the seal established between the ostomy wafer and the stoma. It should be appreciated that the stoma channel structures contemplated herein are generally designed for use with a stoma and are capable of receiving, and/or coming into contact with, internal tissue that may be positioned in the stoma channel when the ostomy wafer is pushed against the stoma. In some embodiments, structures of the stoma channel disclosed herein may define spring-like or accordion-like structures. Additionally, in some embodiments, structures disclosed herein may allow the ostomy wafer to clamp onto a protruding stoma which may preclude use of, or minimize the need for use of, adhesive products.

In some embodiments, structures disclosed herein may prevent the ostomy wafer from dislodging from the stoma. Additionally, in some embodiments, structures disclosed herein may have a spring/rebound property that controls deformation with a predetermined or reference rebound force. It should be appreciated that the structures contemplated by the present disclosure may prevent, or substantially resist, a stoma from slipping out or pulling out of the stoma channel. Additionally, the structures disclosed herein may provide frictional interference between the stoma channel and the stoma, thereby facilitating securement of the ostomy wafer to the stoma.

Non-limiting examples of rigid or semi-rigid materials that may be incorporated into the stoma channel and/or the structures of the stoma channel disclosed herein include hydrocolloid adhesives (e.g., Stomahesive™, Durahesive™, Modified Stomahesive™ Stomahesive™ Seal, Duoderm, or Coloplasts Brava strips), silicone, acrylics, cyanoacrylate (e.g., Liquiband), rubbers, foams, cellulose, polyurethanes, polyethylenes, polyvinyl chlorides, ethylenevinyl acetates, polypropylenes, polytetrafluorethylenes, and polyisobutylenes. In some embodiments, the rigid or semi-rigid materials disclosed herein may be capable of limiting recovery of the adhesive to at least less than 3.175 mm.

In some embodiments, the stoma channels of the ostomy wafers disclosed herein may have different shapes. In one example, the stoma channel may be cylindrical. In another example, the stoma channel may be tapered. In some cases, the stoma channel may be tapered such that the stoma is inserted into the narrow end of the stoma channel. In other cases, the stoma channel may be tapered such that the stoma is inserted into the wide end of the stoma channel. Of course, it should be appreciated that in some embodiments, the stoma channel may not be provided with any structure or structural features other than the structure provided by the layers of the device.

In some embodiments, the stoma channel of the ostomy wafer and areas adjacent thereto may include moldable adhesive technologies. Those adhering features may reduce the number of steps typically required to seal an ostomy wafer to the skin and the stoma of a particular patient. For example, no scissors may be required to cut/tailor the stoma channel to the skin and the stoma of the patient, and there may be no need for additional pastes or adhesives to fill in the contours/structures of the ostomy wafer. Therefore, the ostomy wafers disclosed herein may offer easier and simpler application (and removal) for nurses and patients.

Any ostomy wafer of the present disclosure may include a flange or collar attached to the external layer. In some embodiments, the flange or collar may include additional adhesive for further securing the ostomy wafer to the ostomate and/or sealing the ostomy wafer to the ostomate to resist leakage. Common substances, devices, and/or methods may be employed to securely mate and seal a flange to a stoma, such as applying an adhesive substance (e.g., a paste) around the stoma, at the base of the ileum, and/or at the opening of the ostomy wafer/baseplate as filler for skin folds, uneven skin surfaces, and scars, for example. Other methods may involve using silicone gel to fill uneven skin surfaces, applying the gel directly around the stoma, and applying a wafer/baseplate directly onto the gel. According to such methods, the gel may cure underneath the wafer/baseplate during normal wear time. Non-limiting examples of pastes include ConvaTec's Stomahesive™ paste, Adapt Paste (Hollister), Brava Paste (Coloplast), Securiti-T Stoma Paste (Genairex), MicroHesive Stoma Paste (Cymed), and Osto Stoma Paste (Montreal Osto). Gels include, but are not limited to, Silicone Gel (Trio), and Osto Paste (Stoma-Tech). Additionally, in some embodiments, ingredients of the pastes/gels may include, but are not limited to, Sodium Carboxymethylcellulose, Thixcin, Gelatin, and Pectin.

The ostomy wafers of the present disclosure may include one or more coupling components (e.g., the coupling component 202) to couple or adhere the ostomy wafer to an ostomy pouch. The coupling component(s) may be attached to any ostomy wafer disclosed herein. In some embodiments, the coupling component(s) may be included in the ostomy wafer or any layer thereof. In any case, it should be appreciated that the coupling component(s) are adapted to mechanically connect the ostomy wafer to the ostomy pouch, such as via adhesion by an adhesive layer applied to, coupled to, or otherwise incorporated into, the ostomy wafer and/or the ostomy pouch, or by interaction with one or more additional components. Of course, in other embodiments, the ostomy wafer may not include coupling component(s). In such embodiments, the ostomy wafer may contact the pouch directly or may contact a coupling feature of the pouch.

Ostomy Devices

Ostomy devices of the present disclosure include an ostomy pouch and any one of the ostomy wafers disclosed herein. In some embodiments, the ostomy device may include one or more coupling components (e.g., the component 202 shown in FIG. 2) configured for interaction with the ostomy pouch and/or the ostomy wafer to operatively couple the ostomy pouch and the ostomy wafer in use thereof.

In some embodiments, the coupling component(s) may include, be embodied as, or otherwise provide, a limited motion connection between the ostomy wafer and the ostomy pouch that permits relative displacement between substantially the entire ostomy wafer and the entrance aperture of the ostomy pouch. In such embodiments, the limited motion connection may guide relative displacement between the wafer and the pouch along a limited motion locus. More specifically, in some embodiments, the limited motion connection may guide movement of the wafer relative to the pouch (or vice versa) between an operative position and an access position. In the operative position, the ostomy wafer may be superposed around the entrance aperture of the ostomy pouch. Additionally, in the operative position, an adaptable region of the ostomy wafer may be shrouded by the ostomy pouch on the non-body-facing side and the wafer and pouch may be fixed to one another with a fixation coupling. In the access position, access is provided to the adaptable region from the non-body-facing side.

The coupling component(s) contemplated herein may guide alignment of, or movement between, the ostomy wafer and the ostomy pouch to the operative position, thereby facilitating use for some users, such as elderly, non-dexterous, or visually impaired persons, for example. At the same time, the limited motion connection may permit relative displacement of substantially the entire ostomy wafer with respect to the entrance aperture as discussed above, thereby facilitating conformance of the ostomy wafer to the size and/or shape of the user's stoma, at least in some embodiments. In some embodiments, the limited motion connection may include an articulating link that defines the limited motion locus.

In some embodiments, the ostomy device may be provided as a one-piece component to enhance access thereto and avoid complications such as wholly or partly immovable ostomy wafers, for example. The ostomy wafer may be permanently attached to the ostomy pouch directly or indirectly via the coupling component(s) (which may be permanently attached to the ostomy pouch). For the purposes of the present disclosure, the term "permanently attached" (or like phrases) means that the pieces may be attached with sufficient force that separation of the pieces results in breakage or damage complicating reattachment without additional equipment. Of course, it should be apparent from the teachings of the present disclosure that the ability to displace the ostomy wafer relative to the entrance aperture of the ostomy pouch may permit easier adaptation of the ostomy wafer (e.g., by forming, cutting, or shaping the stomal aperture, or by fitting and/or shaping a separate sealing member at the stomal aperture) to the ostomy pouch.

In some embodiments, the ostomy device may be a two-piece ostomy device. The components of the two-piece device may be aligned without significantly reducing access to the ostomy wafer to facilitate adaption of the ostomy wafer to the size and/or shape of stoma. Additionally, the components may be positioned relative to one another without detracting from the ability to position the body-fitment component on the body before fixing the other component in the operative position with respect to the body fitment component. In some embodiments, the limited motion connection and the coupling component(s) may include releasable coupling portions.

Methods of Use

Further disclosed herein are methods of using the ostomy wafers and ostomy devices of the present disclosure. In some embodiments, the methods may include contacting the flush/retracted stoma with the ostomy wafer. Additionally, in some embodiments, the methods may include contacting the ostomy wafer with an ostomy pouch, cap, or plug that fills any one of the opening(s) of the ostomy wafer. In some embodiments still, the methods may include contacting the flush/retracted stoma or the ostomy wafer with an adhering substance that promotes adherence of the ostomy wafer to the ostomate. In some embodiments yet still, the methods may include contacting the flush/retracted stoma or the ostomy wafer with an additional adhesive besides the adhesive(s) that is a component of the ostomy wafer. Further, in some embodiments, the methods may include applying heat to mold the ostomy wafer or promote the adherent property of the additional adhesive. Further, in some embodiments still, the methods do not require a user to measure, size, fit, cut, or tear the device. Rather, in such embodiments, the user only need mold the device with their fingers to adapt to it to the stoma.

Kits

The kits of the present disclosure include any one of the ostomy wafers disclosed herein. In some embodiments, the kits may also include a kit component selected from an ostomy pouch, a viscous media, an adhesive seal, an adhesive barrier, an adhesive strip, an adhesive fabric, an adhesive paste, and combinations thereof.

EXAMPLES

The examples and embodiments described herein are for illustrative purposes only and are not intended to limit the scope of the claims. It should be appreciated that various modifications or changes apparent to persons skilled in the art are within the spirit and purview of this application and scope of the appended claims.

Example 1: Application of a Pre-Filled Perforated Chamber Ostomy Wafer

An ostomate with a flush or recessed stoma ensures that his/her hands and the skin surrounding the stoma are clean, dry, and free from any solvent or oily substances before applying the ostomy wafer. A perforated chamber ostomy wafer (e.g., one of the wafers 100, 200, 500) with an adhesive paste (e.g., viscous media 150) is removed from packaging. One or more chambers (e.g., the chamber 140) containing the adhesive paste are contained within a pliable, flexible, and perforated convex layer (e.g., the convex layers 120, 220, 520).

A release liner is removed from the perforated chamber wafer (e.g., from a skin barrier thereof) and the opening (e.g., the proximal opening 162) of the perforated chamber wafer is centered over the stoma. The perforated chamber wafer is then pressed into the stoma opening until an external layer of the wafer (e.g., the external layer 110, 210, 510) is flush with external skin surrounding the stoma. As is the perforated chamber wafer is compressed into and around the stoma, the adhesive paste is extruded through the perforations (e.g., the perforations 170) and out of the one or more chambers, thereby filling irregular contours and indentations of the skin to adhere the wafer to the ostomate and provide a secure seal.

To remove the perforated chamber wafer after use, the ostomy wafer is gently peeled from the body. Any residue can be removed from the skin by rolling and peeling, or by using Sensi-Care or Niltac Sting Free Adhesive Remover.

Example 2: Application of an Empty Perforated Chamber Ostomy Wafer

An ostomate ensures that his/her hands and the skin surrounding the stoma are clean, dry, and free from any solvent or oily substances before applying the ostomy wafer. A perforated chamber ostomy wafer (e.g., one of the wafers 100, 200, 500) with one or more empty chambers (e.g., the chamber 140) is removed from packaging. The one or more chambers are contained within a pliable, flexible, and perforated convex layer (e.g., the convex layers 120, 220, 520). The convex layer is provided separately from an external layer (e.g., the external layer 110, 210, 510). The convex layer includes a portion at its external rim for receiving and adhering/bonding to the external layer.

A release liner is removed from the convex layer of the wafer (e.g., from a skin barrier thereof) and the opening (e.g., the proximal opening 162) of the convex layer is centered over the stoma. The convex layer is molded to the stoma without measurement or modification to the convex layer due to the moldable character of the convex layer. Once the convex layer is molded to the stoma, an adhesive paste (e.g., viscous media 150) is added to one or more chambers of the convex layer. A second release liner is removed from the external layer and the external layer is applied to the convex layer to create a seal between the convex layer and the external layer and thereby confine the adhesive paste in the chamber(s) of the convex layer. It should be appreciated that the external layer and the convex layer both include adhesive on their skin-facing sides to adhere to the ostomate. Adhesive paste seeps through the perforations (e.g., the perforations 170) and out of the one or more chambers, thereby filling irregular contours and indentations of the skin to adhere the wafer to the ostomate and provide a secure seal.

To remove the perforated chamber wafer after use, the ostomy wafer is gently peeled from the body. Any residue can be removed from the skin by rolling and peeling, or by using Sensi-Care or Niltac Sting Free Adhesive Remover.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

The invention claimed is:

1. An ostomy wafer comprising:
an external layer including a stoma channel to permit the passage of effluent therethrough, wherein the stoma channel extends in an axial direction, wherein the external layer includes an annular base and a pedestal extending outwardly therefrom in the axial direction, and wherein the pedestal at least partially defines the stoma channel; and
a convex layer coupled to the external layer such that the stoma channel extends therethrough, wherein the convex layer is formed to include a plurality of perforations that are spaced in a radial direction from the stoma channel and at least one chamber that is in fluid communication with the plurality of perforations and spaced from the stoma channel in the radial direction, wherein the external layer at least partially closes off the at least one chamber to confine viscous media that may be stored in the at least one chamber and distributed through the plurality of perforations to couple the ostomy wafer to a subject in use thereof.

2. The ostomy wafer of claim 1, wherein the convex layer includes a distal rim and a proximal opening arranged opposite the distal rim, and wherein the convex layer is coupled to the external layer such that the pedestal extends between the proximal opening and the distal rim.

3. The ostomy wafer of claim 2, wherein the distal rim contacts the annular base to close off the at least one chamber.

4. The ostomy wafer of claim 2, wherein a thickness of the convex layer at the proximal opening is greater than a thickness of the convex layer at the distal rim.

5. The ostomy wafer of claim 2, wherein a thickness of the convex layer at the proximal opening is less than a thickness of the convex layer at the distal rim.

6. The ostomy wafer of claim 2, wherein a width of the proximal opening is less than a width of a distal opening defined by the distal rim.

7. The ostomy wafer of claim 1, wherein at least one of the external layer and the convex layer includes an adhesive to adhere the ostomy wafer to the subject.

8. The ostomy wafer of claim 7, wherein the adhesive includes a multi-laminate adhesive.

9. The ostomy wafer of claim 1, wherein at least one of the external layer and the convex layer includes a three layer tri-laminate adhesive structure.

10. The ostomy wafer of claim 1, wherein at least one of the external layer and the convex layer includes a hydrocolloid adhesive.

11. The ostomy wafer of claim 1, wherein at least one of the external layer and the convex layer includes an adhesive that is moldable complementary to a shape of a stoma of the subject.

12. The ostomy wafer of claim 1, wherein the stoma channel includes a structure located on an internal surface of the ostomy wafer that defines the stoma channel, and wherein the structure includes a plurality of angled fins that extend toward a stoma and are shaped to mate with the stoma of the subject.

13. The ostomy wafer of claim 1, wherein the stoma channel includes a structure located interiorly of an internal surface of the ostomy wafer that defines the stoma channel, and wherein the structure is shaped to mate with a stoma of the subject.

14. The ostomy wafer of claim 1, wherein the convex layer extends in a dimension parallel to a flow of effluent through the ostomy wafer over more than half a centimeter.

15. The ostomy wafer of claim 1, wherein the ostomy wafer has a continuous profile, a stepped profile, an inverted profile, or a combination thereof.

16. The ostomy wafer of claim 15, wherein the ostomy wafer has a convex aspect, a concave aspect, a chamfered aspect, or a combination thereof.

17. The ostomy wafer of claim 16, wherein the ostomy wafer has one or more structural features selected from a strut, a fin, a column, a tie, and combinations thereof.

18. The ostomy wafer of claim 1, further comprising an internal layer that at least partially covers an exterior of the convex layer that faces the subject, wherein the internal layer includes a moldable adhesive material.

19. The ostomy wafer of claim 18, wherein the internal layer includes a second plurality of perforations through which viscous media may be distributed to couple the ostomy wafer to the subject.

20. The ostomy wafer of claim 1, wherein the viscous media is selected from a gel and a paste.

21. The ostomy wafer of claim 1, wherein the viscous media includes a hydrocolloid.

22. The ostomy wafer of claim 1, wherein the viscous media includes an adhesive solution that adheres the wafer to the subject.

23. An ostomy device comprising:
an ostomy pouch; and
an ostomy wafer coupled to the ostomy pouch, the ostomy wafer including:
an external layer including a stoma channel to permit the passage of effluent therethrough, wherein the stoma channel extends in an axial direction;
a convex layer coupled to the external layer such that the stoma channel extends therethrough, wherein the convex layer is formed to include a plurality of perforations that are spaced in a radial direction from the stoma channel and at least one chamber that is in fluid communication with the plurality of perforations, and
an internal layer that at least partially covers an exterior of the convex layer that faces a subject, wherein the internal layer includes a moldable adhesive material, and wherein the internal layer includes a second plurality of perforations through which viscous media may be distributed to couple the ostomy wafer to the subject,
wherein the external layer at least partially closes off the at least one chamber to confine viscous media that may be stored in the at least one chamber and distributed through the plurality of perforations to couple the ostomy wafer to the subject in use thereof.

24. The ostomy device of claim 23, wherein the external layer includes an annular base and a pedestal extending outwardly therefrom in the axial direction that at least partially defines the stoma channel, wherein the convex layer includes a distal rim and a proximal opening arranged opposite the distal rim, and wherein the convex layer is coupled to the external layer such that the pedestal extends between the proximal opening and the distal rim.

25. The ostomy device of claim 23, wherein the external layer includes an annular base and a pedestal extending outwardly therefrom in the axial direction that at least partially defines the stoma channel, wherein the convex layer includes a distal rim and a proximal opening arranged opposite the distal rim, and wherein the distal rim contacts the annular base to close off the at least one chamber.

26. The ostomy device of claim 23, wherein the stoma channel includes a structure located on an internal surface of the ostomy wafer that defines the stoma channel, and wherein the structure includes a plurality of angled fins that extend toward a stoma and are shaped to mate with the stoma of the subject.

27. The ostomy device of claim 23, wherein the stoma channel includes a structure located interiorly of an internal surface of the ostomy wafer that defines the stoma channel, and wherein the structure is shaped to mate with a stoma of the subject.

28. The ostomy device of claim 23, wherein the convex layer includes a distal rim and a proximal opening arranged opposite the distal rim, and wherein a thickness of the convex layer at the proximal opening is greater than a thickness of the convex layer at the distal rim.

29. The ostomy device of claim 23, wherein the convex layer includes a distal rim and a proximal opening arranged opposite the distal rim, and wherein a thickness of the convex layer at the proximal opening is less than a thickness of the convex layer at the distal rim.

* * * * *